(12) United States Patent
Xu

(10) Patent No.: US 11,999,998 B2
(45) Date of Patent: Jun. 4, 2024

(54) MODIFICATION OF 5-METHYLCYTOSINE CATALYZED BY Cmd1 ENZYME AND APPLICATION THEREOF

(71) Applicant: Shanghai Institutes for Biological Sciences, Chinese Academy of Sciences, Shanghai (CN)

(72) Inventor: Guoliang Xu, Shanghai (CN)

(73) Assignee: Center for Excellence in Molecular Cell Science, Chinese Academy of Sciences, Shanghai (CN)

( * ) Notice: Subject to any disclaimer, the term of this patent is extended or adjusted under 35 U.S.C. 154(b) by 1502 days.

(21) Appl. No.: 16/327,521

(22) PCT Filed: Aug. 24, 2017

(86) PCT No.: PCT/CN2017/098786
§ 371 (c)(1),
(2) Date: Mar. 15, 2019

(87) PCT Pub. No.: WO2018/036537
PCT Pub. Date: Mar. 1, 2018

(65) Prior Publication Data
US 2023/0183795 A1    Jun. 15, 2023

(30) Foreign Application Priority Data

Aug. 24, 2016 (CN) .......................... 201610719692.4

(51) Int. Cl.
*C12Q 1/6869* (2018.01)
*C12N 9/02* (2006.01)
*C12P 19/34* (2006.01)

(52) U.S. Cl.
CPC ......... *C12Q 1/6869* (2013.01); *C12N 9/0069* (2013.01); *C12P 19/34* (2013.01)

(58) Field of Classification Search
CPC ...... C12Q 1/6869; C12Q 1/6827; C12Q 1/68; C12Q 1/6806; C12N 9/0069; C12P 19/34; C12Y 113/11
See application file for complete search history.

(56) References Cited

FOREIGN PATENT DOCUMENTS

| | | |
|---|---|---|
| CN | 102317473 A | 1/2012 |
| CN | 102888395 A * | 1/2013 |
| CN | 102888395 A | 1/2013 |
| CN | 104694490 A | 6/2015 |
| CN | 104781422 A | 7/2015 |
| CN | 105648537 A | 6/2016 |
| WO | 2012138973 A2 | 10/2012 |
| WO | 2014165770 A1 | 10/2014 |

OTHER PUBLICATIONS

Ehrlich, Melanie, and Richard Y-H. Wang. "5-Methylcytosine in eukaryotic DNA." Science 212.4501 (1981): 1350-1357 (Year: 1981).*
CN-102888395-A, English Translation (Year: 2013).*
Predicted protein [*Chlamydomonas reinhardtii*]. Accession GenBank: EDP03085.1. https://www.ncbi.nlm.nih.gov/protein/EDP03085.1?report=ge . . . Feb. 25, 2019.
Tahiliani et al. Conversion of 5-Methylcytosine to 5 Hydroxymethylcytosine in Mammalian DNA by MLL Partner TET1. Science. May 15, 2009; 324(5929): 930-935. doi:10.1126/science.1170116.
Xu et al. "Genome-wide Regulation of 5hmC, 5mC and Gene Expression by Tet1 Hydroxylase in Mouse Embryonic Stem Cells"; Mol Cell. May 20, 2011; 42(4): 451-464. doi:10.1016/j.molcel.2011.04.005.

* cited by examiner

*Primary Examiner* — Nancy J Leith
*Assistant Examiner* — Kyle Thomas Rega
(74) *Attorney, Agent, or Firm* — Banner & Witcoff, Ltd.

(57) ABSTRACT

The present invention relates to a novel modification of a 5-methylcytosine nucleic acid catalyzed by a Cmd1 enzyme and an application thereof. The present inventors have for the first time discovered Cmd1, a 5mC-modifying enzyme, which can link a glyceryl group to a 5mC methyl carbon of a methylated nucleic acid through a carbon-carbon single bond, and this is a new epigenetic modification.

11 Claims, 10 Drawing Sheets
Specification includes a Sequence Listing.

Fig. 1

SEQUENCE LISTING

<160> NUMBER OF SEQ ID NOS: 16

<210> SEQ ID NO 1
<211> LENGTH: 532
<212> TYPE: PRT
<213> ORGANISM: Chlamydomonas reinhardtii

<400> SEQUENCE: 1

Met Ser Val Ala Leu Ala Ser Glu Tyr Gln Leu Val Gln Asn Ala Gln
1               5                   10                  15

Leu Pro Gln Arg Trp Ser Gln Ser Ala Arg Lys Ser Leu Ala Ile Leu
            20                  25                  30

Glu Ala Thr Ala Arg Lys Glu Ala Thr Ala Gln Met Glu Ala Ala Gly
        35                  40                  45

Gly Ser Phe Cys Gly Gln Phe Pro Val Asp Pro Ala Phe Lys Val Leu
    50                  55                  60

Ser Leu Glu Tyr Ser Ala Pro Asn Pro Asp Ile Ala Arg Ala Ile Arg
65                  70                  75                  80

Arg Val Asp Ser Val Pro Asn Pro Leu Pro Ser His Val Ala
            85                  90                  95

Ile Gln Ser Thr Ala Val Asp Ala Asp Leu Ser Leu Ala Met Gly Val
                100                 105                 110

Ser Leu Thr Pro Gly Arg His Thr Ser Tyr Leu Val Asp Ala Arg Ala
            115                 120                 125

Leu Gln Gln Ser Asn Ser Ala Ala Val Ala Ala Arg Lys Ala Asp Gly
        130                 135                 140

Asp Lys Trp Gly Pro Ala Cys Asp Glu Met Phe Arg Gly Cys Arg Cys
145                 150                 155                 160

Val Thr Gly Gln Glu Val Val Phe Tyr Thr Ala Val Lys Glu Pro Ala
                165                 170                 175

Gly Glu Val Glu Gly Gly Glu Gly Ser Leu Phe Lys Pro Ser Phe Asp
            180                 185                 190

Gly Pro Ala Phe Arg Pro Ser Trp Gly Glu Leu Ser Gly Lys Ala Thr
        195                 200                 205

Gly Val Val Ala Cys Val Leu Gln Val Pro Ile Gly Lys Glu Thr Asp
    210                 215                 220

Ile Ile Cys Ala Glu Tyr Asp Asn Leu Val Ser Lys Gly Gln Phe Ala
225                 230                 235                 240

Thr Val Asp Arg Phe Gly Gly Asp His Thr Val Asn Met Thr Gly Asn
                245                 250                 255

Ala Leu Ile Gln Asn Asp Gly Lys Ala Ile Ser Lys Gly Tyr Ala Val
            260                 265                 270

Ala His Arg Ala Arg Val Thr Ser Asn Val Tyr Gly Lys Ala Asn Asp
        275                 280                 285

Val Ser Leu Gln Arg Leu Ala Gly Thr Val Trp Ser Val Val Glu Lys
    290                 295                 300

Arg Leu Ser Phe Met Pro Ala Tyr Arg Asp Leu Val Ile Thr Glu Gln
305                 310                 315                 320

Gly Lys Pro Phe Met Leu Gly Ala Thr Ala Thr Asn Ile Ile Ser Leu
                325                 330                 335

Thr Glu Asn Gln Gly Val Met Leu His Leu Asp Thr Asp Gly Val
            340                 345                 350

Trp Thr Ile Ile Leu Trp Phe His Arg His Ser Gly Ile Ile Ala Gly
        355                 360                 365

-continued

Gly Glu Phe Val Leu Pro Ser Leu Gly Ile Ser Phe Gln Pro Leu Asp
          370                 375                 380

Phe Thr Ile Val Val Phe Ala Ala Asn Thr Ile Val His Gly Thr Arg
385                 390                 395                 400

Pro Leu Gln Thr Thr Gly Lys Ile Ile Arg Trp Gly Ser Ser His Phe
              405                 410                 415

Leu Arg Phe Lys Asp Val Asn Ala Leu Ala Gln Leu Gly Ala Ala Tyr
              420                 425                 430

Gly Val Asp Glu Leu Asp Ala Lys Gln Arg Asp Gln Leu Glu Glu Val
              435                 440                 445

Asp Ala Ala Asn Ser Lys Asp Gly Val Gly Ala Ala Arg Arg Val Ala
          450                 455                 460

Ser Cys Met Ala Ala Glu Arg Lys Ala Ala Ile Glu Ala Gln Lys Ala
465                 470                 475                 480

Ala Cys Val Arg Gly Val Val Met Asn Pro Cys Thr Gly Arg Met Pro
              485                 490                 495

Ser Leu Leu Phe Trp Gln Val Trp Arg Lys Pro Pro Ala Leu Ala Val
              500                 505                 510

Arg Ala Asn Ala Val Ala Gly Lys Lys Arg Ala Ala Asp Val Asp
              515                 520                 525

Phe Cys Gly Ala
    530

<210> SEQ ID NO 2
<211> LENGTH: 25
<212> TYPE: DNA
<213> ORGANISM: artificial sequence
<220> FEATURE:
<221> NAME/KEY: misc_feature
<223> OTHER INFORMATION: polynucleotide

<400> SEQUENCE: 2
atcaggaaac caaggcgcgc tagct                                       25

<210> SEQ ID NO 3
<211> LENGTH: 54
<212> TYPE: DNA
<213> ORGANISM: artificial sequence
<220> FEATURE:
<221> NAME/KEY: misc_feature
<223> OTHER INFORMATION: polynucleotide

<400> SEQUENCE: 3
gtactgcagc tggaacactg cgcccaggaa gctagcgcgc cttggttttcc tgat      54

<210> SEQ ID NO 4
<211> LENGTH: 50
<212> TYPE: DNA
<213> ORGANISM: artificial sequence
<220> FEATURE:
<221> NAME/KEY: misc_feature
<223> OTHER INFORMATION: polynucleotide

<400> SEQUENCE: 4
tcctgggcgc agtgttccag ctgcagtacg gggtccttat tcaaggcata            50

<210> SEQ ID NO 5
<211> LENGTH: 42
<212> TYPE: DNA
<213> ORGANISM: artificial sequence
<220> FEATURE:
<221> NAME/KEY: misc_feature -continued
<223> OTHER INFORMATION: polynucleotide

<400> SEQUENCE: 5
ccatggtgcc gatcagcgag atatgccttg aataaggacc cc         42

<210> SEQ ID NO 6
<211> LENGTH: 42
<212> TYPE: DNA
<213> ORGANISM: artificial sequence
<220> FEATURE:
<221> NAME/KEY: misc_feature
<223> OTHER INFORMATION: polynucleotide

<400> SEQUENCE: 6
tctcgctgat cggcaccatg ggggtggtgg tgatcagcgc ta         42

<210> SEQ ID NO 7
<211> LENGTH: 42
<212> TYPE: DNA
<213> ORGANISM: artificial sequence
<220> FEATURE:
<221> NAME/KEY: misc_feature
<223> OTHER INFORMATION: polynucleotide

<400> SEQUENCE: 7
ggggtcctta ttcaagccat atagcgctga tcaccaccac cc         42

<210> SEQ ID NO 8
<211> LENGTH: 47
<212> TYPE: DNA
<213> ORGANISM: artificial sequence
<220> FEATURE:
<221> NAME/KEY: misc_feature
<223> OTHER INFORMATION: polynucleotide

<400> SEQUENCE: 8
tatggcttga ataaggaccc ctactgcagc cggaacactg ccaggag    47

<210> SEQ ID NO 9
<211> LENGTH: 30
<212> TYPE: DNA
<213> ORGANISM: artificial sequence
<220> FEATURE:
<221> NAME/KEY: misc_feature
<223> OTHER INFORMATION: polynucleotide

<400> SEQUENCE: 9
aattctcctg gcagtgttcc ggctgcagta                      30

<210> SEQ ID NO 10
<211> LENGTH: 168
<212> TYPE: DNA
<213> ORGANISM: artificial sequence
<220> FEATURE:
<221> NAME/KEY: misc_feature
<223> OTHER INFORMATION: polynucleotide

<400> SEQUENCE: 10
atcaggaaac caaggcgcgc tagcttcctg ggcgcagtgt tccagctgca gtacggggtc    60
cttattcaag gcatatctcg ctgatcggca ccatgggggt ggtggtgatc agcgctatat   120
ggcttgaata aggacccct ctgcagccgg aacactgcca ggagaatt                 168

<210> SEQ ID NO 11
<211> LENGTH: 29
<212> TYPE: DNA

```
<210> SEQ ID NO 11
<211> LENGTH: 29
<212> TYPE: DNA
<213> ORGANISM: artificial sequence
<220> FEATURE:
<221> NAME/KEY: misc_feature
<223> OTHER INFORMATION: primer

<400> SEQUENCE: 11
aagggttgga ttgtaggtag tttagaaat                                  29

<210> SEQ ID NO 12
<211> LENGTH: 17
<212> TYPE: DNA
<213> ORGANISM: artificial sequence
<220> FEATURE:
<221> NAME/KEY: misc_feature
<223> OTHER INFORMATION: primer

<400> SEQUENCE: 12
tgagggtggt aaattag                                               17

<210> SEQ ID NO 13
<211> LENGTH: 23
<212> TYPE: DNA
<213> ORGANISM: artificial sequence
<220> FEATURE:
<221> NAME/KEY: misc_feature
<223> OTHER INFORMATION: primer

<400> SEQUENCE: 13
ccacaaacat catctctctc acc                                        23

<210> SEQ ID NO 14
<211> LENGTH: 21
<212> TYPE: DNA
<213> ORGANISM: artificial sequence
<220> FEATURE:
<221> NAME/KEY: misc_feature
<223> OTHER INFORMATION: primer

<400> SEQUENCE: 14
atggtgaagt ccagtggttg a                                          21

<210> SEQ ID NO 15
<211> LENGTH: 20
<212> TYPE: DNA
<213> ORGANISM: artificial sequence
<220> FEATURE:
<221> NAME/KEY: misc_feature
<223> OTHER INFORMATION: primer

<400> SEQUENCE: 15
gtcatccact gcctgtgctt                                            20

<210> SEQ ID NO 16
<211> LENGTH: 20
<212> TYPE: DNA
<213> ORGANISM: artificial sequence
<220> FEATURE:
<221> NAME/KEY: misc_feature
<223> OTHER INFORMATION: primer

<400> SEQUENCE: 16
ccttcttgct ggtgatgttg                                            20
```

MODIFICATION OF 5-METHYLCYTOSINE CATALYZED BY Cmd1 ENZYME AND APPLICATION THEREOF

TECHNICAL FIELD

The present invention belongs to the field of epigenetics, and more specifically, relates to a novel modification of a 5-methylcytosine nucleic acid catalyzed by a Cmd1 enzyme and an application thereof.

SEQUENCE LISTING

The instant application contains a Sequence Listing which has been submitted electronically in ASCII format and is hereby incorporated by reference in its entirety. Said ASCII copy, created on Jan. 30, 2024, is named Sequence Listing_008703_00013_US_SL_updated.txt and is 45,056 bytes in size.

BACKGROUND

As a nucleic acid modification widely distributed among plants and animals, 5-methylcytosine (5mC) is closely related to various biological processes such as epigenetic regulation. In mammals, 5mC can be oxidized by a Tet dioxygenase to form 5-hydroxymethylcytosine (5hmC), 5-formylcytosine (5fC) and 5-carboxycytosine (5caC). However, 5fC and 5caC can be specifically recognized and excised by a TDG glycosidase. In *Arabidopsis*, 5mC can be directly excised by a specific glycosidase to form an AP site. These processing processes of 5mC all participate in or promote the demethylation of nucleic acids to some extent. 5mC and similar derivatization modifications are also present in organisms including amoeba, *Coprinus cinereus*, etc., but whether there are other different 5mC derivatization modifications requires further study.

Using the evolutionarily conserved Tet-JBP domain as a template, homologous proteins of the Tet dioxygenase have been found in a variety of species. The present inventors have identified 8 Tet homologous proteins (CrTet1-8, FIG. 1) in *Chlamydomonas reinhardtii* using Phytozome database. *Chlamydomonas reinhardtii* belongs to Chlorophyta phylum, is relatively primitive in evolution, and is considered to be the ancestor of many plants. The present inventors have found the 8 Tet homologous proteins all have an HxD motif consistent with mammalian and amoeba Tet proteins, which may be responsible for binding to $Fe^{2+}$. Although α-ketoglutaric acid (2-OG) is involved in an enzymatic activity reaction as an essential cofactor for many dioxygenase families, the present inventors did not found a 2-OG binding site in these proteins, suggesting that these proteins may have a distinctive feature.

Therefore, it is necessary in the art to study the enzymatic activity of these proteins, find their new functions, and develop new applications for them.

SUMMARY OF THE INVENTION

The purpose of the present invention is to provide a novel modification of a 5-methylcytosine nucleic acid catalyzed by a Cmd1 enzyme and an application thereof.

In the first aspect, the present invention provides a method for adding a glyceryl group to a methyl group of 5-methylcytosine (5mC) of a methylated nucleic acid, comprising: treating the methylated nucleic acid with a Cmd1 enzyme, so that the glyceryl group is added to the methyl group of 5-methylcytosine (5mC) of the methylated nucleic acid.

In one preferred embodiment, a glyceryl group-containing compound is used as a glyceryl group donor.

In another preferred embodiment, the glyceryl group-containing compound is vitamin C or its analogue.

In another preferred embodiment, the vitamin C analogue comprises dehydroascorbic acid.

In another preferred embodiment, in a reaction system in which the methylated nucleic acid is treated with the Cmd1 enzyme, a ferrous ion ($Fe^{2+}$) is present as a cofactor.

In another preferred embodiment, the method for adding a glyceryl group to a methyl group of 5-methylcytosine (5mC) of a methylated nucleic acid is a non-diagnostic and therapeutic method.

In another preferred embodiment, the method for adding a glyceryl group to a methyl group of 5-methylcytosine (5mC) of a methylated nucleic acid is an in vitro method.

In another preferred embodiment, the methylated nucleic acid is treated with the Cmd1 enzyme, thereby forming a product selected from the following (the product is present on the nucleic acid strand).

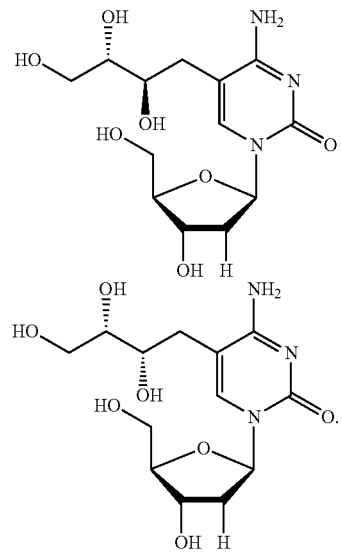

In another preferred embodiment, the Cmd1 enzyme is a Cmd1 enzyme derived from algae; preferably, the alga is *Chlamydomonas* or Volvox.

In another preferred embodiment, the Cmd1 enzyme comprises: (a) a polypeptide of an amino acid sequence of SEQ ID NO: 1; (b) a polypeptide derived from (a), being formed by subjecting the amino acid sequence of SEQ ID NO: 1 to substitution, deletion or addition of one or more (such as 1-30; preferably 1-20; more preferably 1-10; such as 5 and 3) amino acid residues, and having the function of the polypeptide of (a); or (c) a polypeptide derived from (a), having more than 60% (preferably more than 70%, such as 80%, 85%, 90%, 95%, 98%, 99% or higher) homology to the polypeptide sequence defined in (a) and having the function of the polypeptide of (a);

and moreover, in the sequences defined in (b) and (c), based on the amino acid sequence of SEQ ID NO: 1, the 330th position is A, the 345th position is H, the 347th position is D, and the 350th position is D.

In another aspect, the present invention provides the use of the Cmd1 enzyme or its up-regulator for adding one glyceryl group to a methyl group of 5-methylcytosine (5mC) of a methylated nucleic acid or for preparing a formulation for adding one glyceryl group to a methyl group of 5-methylcytosine (5mC) of a methylated nucleic acid. Preferably, the glyceryl group is derived from a glyceryl group-containing compound, such as vitamin C or its analogue.

In one preferred embodiment, the up-regulator of the Cmd1 enzyme is an expression vector useful in the recombinant expression of the Cmd1 enzyme, for example, a pET28a vector, which contains a gene expression cassette for the Cmd1 enzyme.

In another preferred embodiment, the glyceryl group is attached to the carbon atom of the methyl group of 5-methylcytosine via a carbon-carbon single bond.

In another aspect, the present invention provides the use of a Cmd1 enzyme down-regulator for reducing the level of a modified methylated nucleic acid which is a methylated nucleic acid carrying a glyceryl group on the methyl group of 5-methylcytosine.

In one preferred embodiment, the Cmd1 enzyme down-regulator is a substance which reduces the gene expression or activity of Cmd1; preferably, the Cmd1 enzyme down-regulator is an interfering molecule which specifically interferes with the gene expression of Cmd1, or is an antibody that specifically inhibits the activity of the Cmd1 enzyme; more preferably, the interfering molecule is a microRNA or a precursor thereof, a dsRNA, an antisense nucleic acid or a small interfering RNA which inhibits or silences the Cmd1 gene or a transcript thereof, or a construct capable of expressing or forming said microRNA or precursor thereof, dsRNA, antisense nucleic acid or small interfering RNA.

In another preferred embodiment, the Cmd1 enzyme down-regulator is an expression vector comprising the sequence of SEQ ID NO: 10 (Cmd1 amiRNA precursor).

In another preferred embodiment, the use of the Cmd1 enzyme or its up-regulator or down-regulator is a non-diagnostic and therapeutic use.

In another aspect, the present invention provides a Cmd1 enzyme down-regulator which is an expression vector comprising the sequence of SEQ ID NO: 10 (Cmd1 amiRNA precursor).

In another aspect, the present invention provides the use of a glyceryl group-containing compound for use in the process of adding a glyceryl group to a methyl group of 5-methylcytosine of a methylated nucleic acid for a Cmd1 enzyme as a glyceryl group donor. For example, the glyceryl group-containing compound is vitamin C or its analogue.

In one preferred embodiment, the use of the glyceryl group-containing compound is a non-diagnostic and therapeutic use.

In another aspect, the present invention provides a method for identifying a methylated nucleic acid, the method comprising:
(1) treating the nucleic acid to be detected (e.g., genomic DNA) with a Cmd1 enzyme, thereby adding a glyceryl group to a methyl group of 5-methylcytosine (5mC) of the methylated nucleic acid therein; and
(2) identifying a product in which a glyceryl group modification occurs from the reaction product so as to determine the presence or amount of the methylated nucleic acid.

In one preferred embodiment, in the step (1), a glyceryl group-containing compound is present as a glyceryl group donor, and a ferrous ion ($Fe^{2+}$) is present as a cofactor; preferably, the glyceryl group-containing compound is vitamin C or its analogue.

In another preferred embodiment, the glyceryl group is labeled; preferably, the label is a $^{13}C$ isotope label.

In another preferred embodiment, the method for identifying a methylated nucleic acid is a non-diagnostic and therapeutic method.

In another aspect, the present invention provides a single-base detection method for detecting gene modification on the methylated nucleic acid, the method comprising:
(a) treating the nucleic acid to be detected with a Tet dioxygenase, so that 5-methylcytosine (5mC), 5-hydroxymethylcytosine (5hmC) and 5-formylcytosine (5fC) are all oxidized to 5-carboxycytosine (5caC), whereas 5-methylcytosine (5mC) with a glyceryl group modification is not oxidized; and
(b) distinguishing the deaminated 5-methylcytosine, etc. in the nucleic acid to be detected from the 5-methylcytosine that has not been converted due to a glyceryl group modification by using bisulfite sequencing for determination.

In one preferred embodiment, the single-base detection method for detecting gene modification on the methylated nucleic acid is a non-diagnostic and therapeutic method.

In another aspect, the present invention provides a single-base detection method, the method comprising:
(S1) sequencing the nucleic acid to be detected by a third-generation or updated nucleic acid sequencing method to distinguish a cytosine from the 5-hydroxymethylcytosine (5hmC), 5-formylcytosine (5fC) and 5-carboxycytosine (5caC) in the nucleic acid to be detected; preferably, the third-generation or updated nucleic acid sequencing method includes, but not limited to, SMRT sequencing or nanopore sequencing;
(S2) treating the nucleic acid to be detected with Cmd1 to add a glyceryl group to a methyl group of 5-methylcytosine (5mC), so as to distinguish 5-methylcytosine (5mC) in the nucleic acid to be detected.

In another aspect, the present invention provides a method for distinguishing 5-methylcytosine (5mC) from 5-hydroxymethylcytosine (5hmC) in a nucleic acid to be detected where no 5-methylcytosine (5mC) modified by a glyceryl group is present in the nucleic acid to be detected, the method comprising:
(i) treating the nucleic acid to be detected with a Cmd1 enzyme so that 5-methylcytosine (5mC) is converted to a 5-methylcytosine (5mC) modified by a glyceryl group, and 5-hydroxymethylcytosine (5hmC) cannot be modified by a glyceryl group;
(ii) treating the product of the step (i) with a Tet dioxygenase, so that 5-hydroxymethylcytosine (5hmC) is oxidized to 5-carboxycytosine (5caC), whereas the 5-methylcytosine (5mC) modified by a glyceryl group is not oxidized, thereby distinguishing 5-methylcytosine (5mC) from 5-hydroxymethylcytosine (5hmC) in the nucleic acid to be detected, preferably by the bisulfite-seq method.

In one preferred embodiment, the method for distinguishing 5-methylcytosine from 5-hydroxymethylcytosine in the nucleic acid to be detected is a non-diagnostic and therapeutic method.

In another aspect, the present invention provides a method for determining the presence or absence of the glyceryl group-containing compound in a sample to be detected, the method comprising: adding a Cmd1 enzyme and a 5mC-containing nucleic acid to the sample to be detected, and determining whether a glyceryl group is added to a methyl group of 5-methylcytosine (5mC) of the methylated nucleic acid; if so, it indicates that the glyceryl group-containing compound is present in the sample to be detected. For example, the glyceryl group-containing compound is vitamin C or its analogue.

In another aspect, the present invention provides a method of targeted regulation of gene expression, the method comprising: treating the target gene with a Cmd1 enzyme so as to add a glyceryl group to a methyl group of 5-methylcytosine of the methylated nucleic acid to obtain a gene in which 5-methylcytosine is modified by a glyceryl group, wherein the expression of this gene has been changed compared to that before the Cmd1 enzyme treatment. The method of targeted regulation of gene expression can be used for transcriptional regulation of cells; preferably, for specifically inhibiting protooncogenes or other pathogenic genes; or for controlling gene expression and regulating cell differentiation, etc.

In another aspect, the present invention provides a method for affecting protein binding or enzymatic activity by altering the modified form of a cellular genome or in vitro nucleic acid, characterized in that the method comprises: treating a cellular endogenous genome or in vitro nucleic acid with a Cmd1 enzyme, thereby adding a glyceryl group to a methyl group of 5-methylcytosine of the methylated nucleic acid therein, obtaining 5-methylcytosine modified by a glyceryl group, and thereby affecting the binding of the cellular genome or in vitro nucleic acid to a protein, or affecting the function of the enzyme on the cellular genome or in vitro nucleic acid. For example, the enzyme is a restriction enzyme; more specifically, for example, MspI.

In another aspect, the present invention provides a kit for adding a glyceryl group to a methyl group of 5-methylcytosine of the methylated nucleic acid, the kit comprising: a Cmd1 enzyme or its up-regulator; a glyceryl group-containing compound; preferably, the glyceryl group-containing compound is vitamin C or its analogue, or a substance capable of generating VC; and a ferrous ion or a substance capable of forming a ferrous ion.

Other aspects of the present invention will be apparent to a person skilled in the art from this disclosure.

BRIEF DESCRIPTION OF THE DRAWINGS

Figure 1:
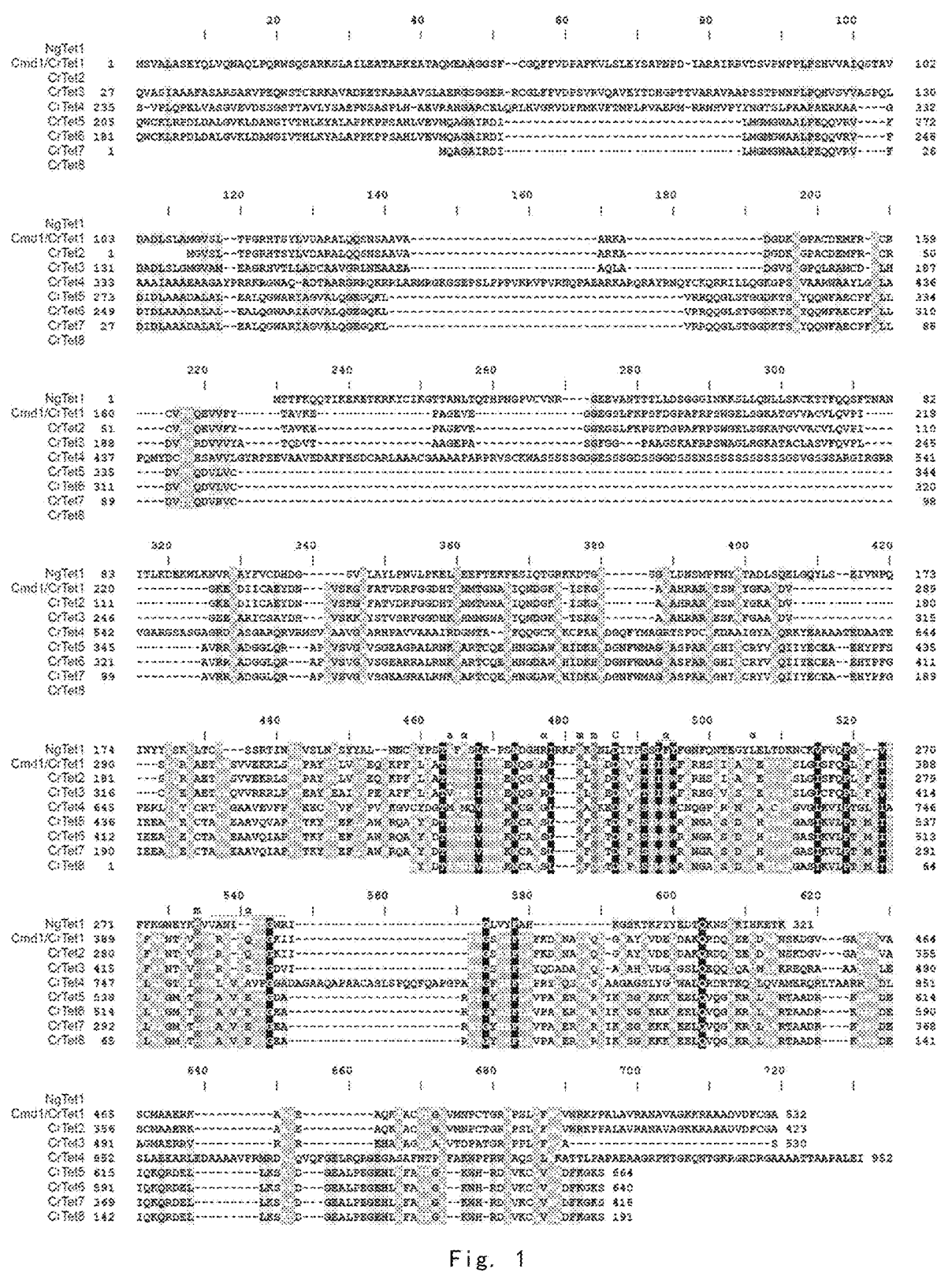

FIG. 1. Amino acid sequence alignment map of Tet homologous proteins in *Chlamydomonas reinhardtii* and amoeba Tet1. The eight *Chlamydomonas* Tet homologous proteins were obtained by alignment of the Tet-JBP domain in the *Chlamydomonas* genome, which, like the Tet proteins in the amoeba and mammals, all have a conserved HxD motif. The label above the sequence indicates that the amino acid residue at this position has been verified for specific functions in NgTet1 structure and biochemical analysis: "m" indicates a metal ion (a ferrous ion) binding site, "C" indicates a site of interaction with 5mC, "a" indicates an active center site, and "α" indicates an α-ketoglutarate binding site. The α-ketoglutarate binding site is not conserved in the *Chlamydomonas* Tet homologous protein CrTet1 (Cmd1). The amino acid sequences of Tet homologous proteins in the alignment map from top to bottom in order of appearance correspond to NgTet1 (SEQ ID NO: 17), Cmd1/CrTet1 (SEQ ID NO: 18), CrTet2 (SEQ ID NO: 19), CrTet3 (SEQ ID NO: 20), CrTet4 (SEQ ID NO: 21), CrTet5 (SEQ ID NO: 22), CrTet6 (SEQ ID NO: 23), CrTet6 (SEQ ID NO: 23), CrTet7 (SEQ ID NO: 24), and CrTet8 (SEQ ID NO: 25).

A: Coomassie blue staining image of the label-free Cmd1 purified from *E. coli*. The image shows the Cmd1 proteins in different collection tubes (14-17 min, 1 ml/min) in gel filtration chromatography.

B: HPLC analysis of DNA components after incubation of 5mC-DNA with Cmd1 proteins. P1/P2 represents two newly detected peaks different from the standard. Mut Cmd1 is an enzymatic activity mutant of Cmd1 containing two point mutations (H345Y/D347A).

C: HPLC results showed that the products P1 and P2 accumulated continuously and gradually reached the plateau during the first two hours of incubation of the 5mC-DNA substrate with Cmd1.

Figure 2:
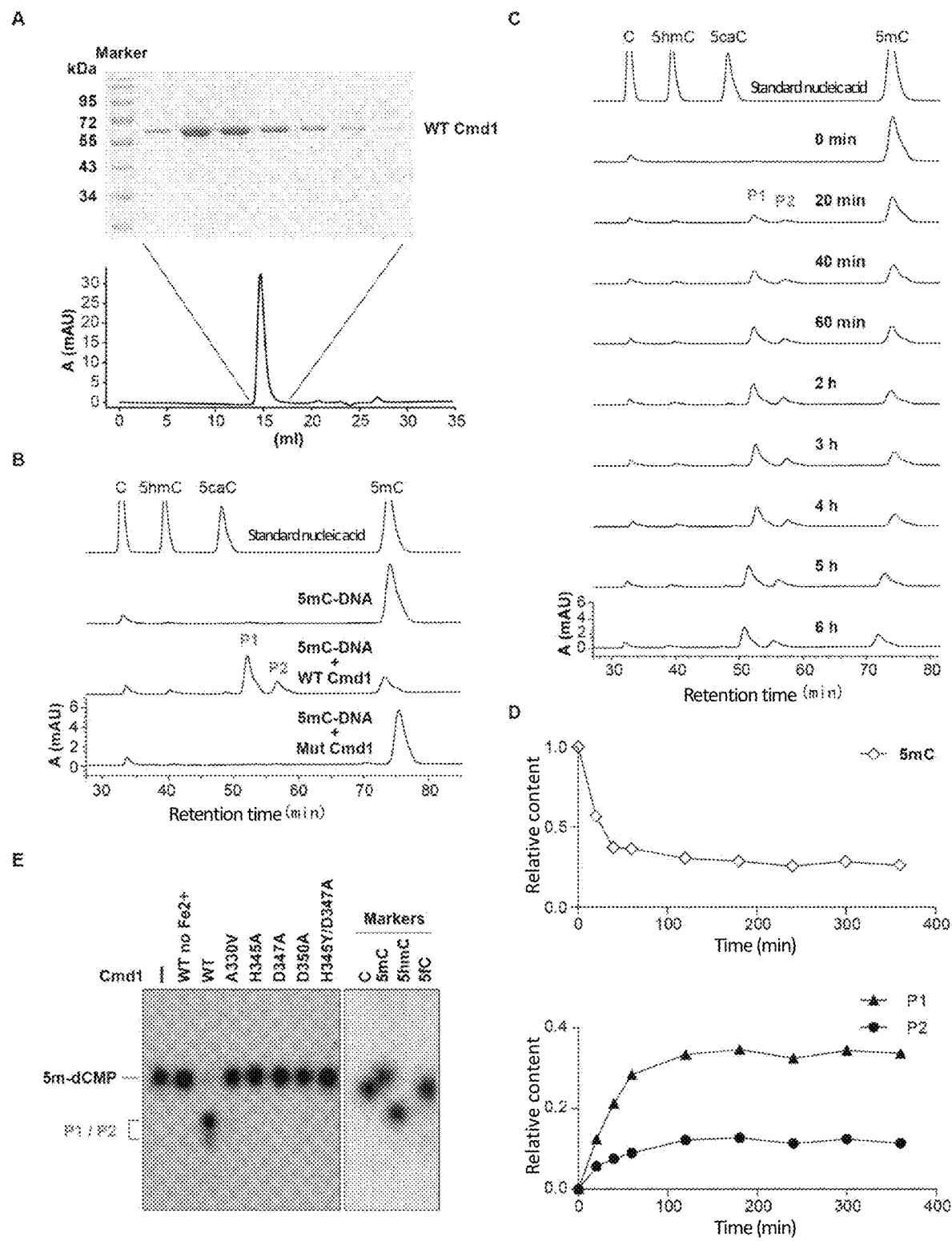
FIG. 2. Formation of new DNA modifications by Cmd1 catalyzing 5mC.

D: Time curve of the Cmd1 enzymatic activity reaction, wherein the relative contents of 5mC, P1 and P2 were calculated from the HPLC peak area (FIG. 2C).

E: TLC detection of the nucleoside component of 5mC-DNA modified by Cmd1. The methyl group of 5mC is labelled with $^{14}C$ and then reacted with wild-type or mutant Cmd1. P1/P2 represents the new modification point detected on the TLC plate.

Figure 3:
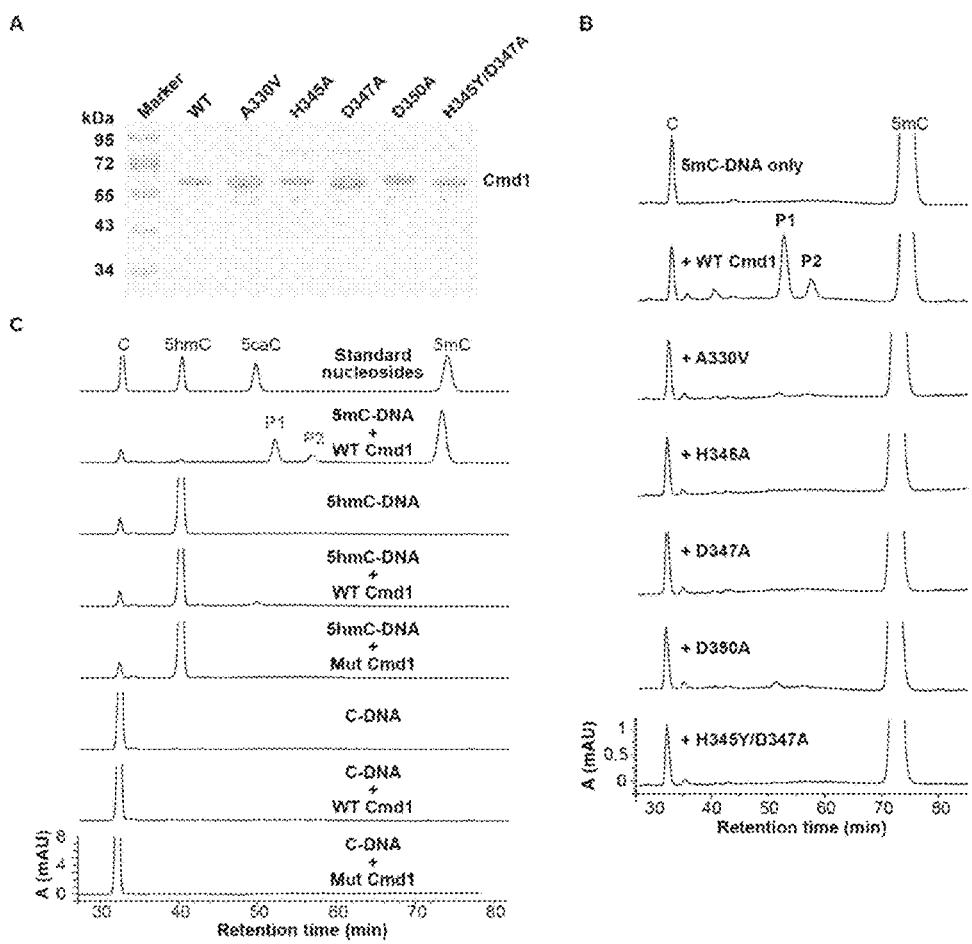

FIG. 3. Lost of most or all of the enzymatic activity of Cmd1 when the predicted functional amino acid residues are mutated.

A: Coomassie blue staining image of purified Cmd1 and its mutants in *E. coli*. According to the results of sequence alignment, it is suggested that H345 and D347 are sites that bind to a ferrous ion, A330 is the center site of the enzymatic activity of Cmd1, and D350 interacts with 5mC.

B: The Cmd1 mutants almost lost the enzymatic activity for catalyzing 5mC to P1 or P2.

C: DNA containing 5mC instead of C or 5hmC can serve as a substrate for the Cmd1 catalytic reaction. The DNA containing C, 5hmC or 5mC was obtained by PCR amplification, and after incubated with Cmd1, the nucleoside composition was determined by HPLC. The P1 and P2 nucleosides were detected during the incubation of the DNA containing 5mC with wild-type Cmd1 (WT Cmd1), and the key region-mutated Cmd1 lost activity. Mut Cmd1 is an enzymatic activity mutant of Cmd1, the protein sequence of which contains two point mutations (H345Y/D347A).

Figure 4:
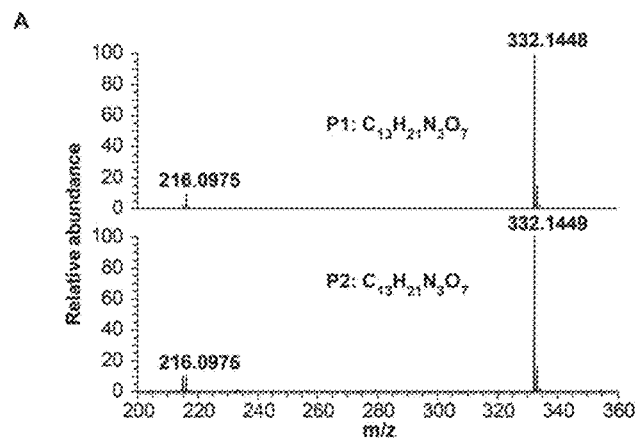
Figure 4:
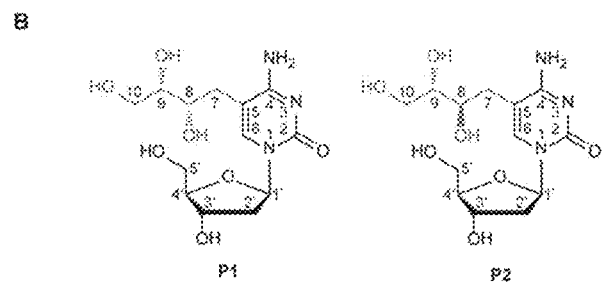

FIG. 4. Analysis of the molecular formula and the structural formula of P1/P2.

A: Mass spectrometry detection of the relative molecular mass of P1/P2 nucleoside. The P1/P2 nucleoside was obtained by catalyzing 5mC-DNA in vitro by Cmd1, enzymatically hydrolyzed, and separated by HPLC. The 216.0976 peak corresponds exactly to the molecular weight of the base portion of the nucleoside P1/P2 (332.1448, theoretically) remaining after neutral loss of deoxyribose (116).

B: Structural formula of P1/P2 determined according to two-dimensional nuclear magnetic resonance and density functional theory. P1 and P2 are stereoisomers with chiral differences only at the C8 position.

Figure 5:
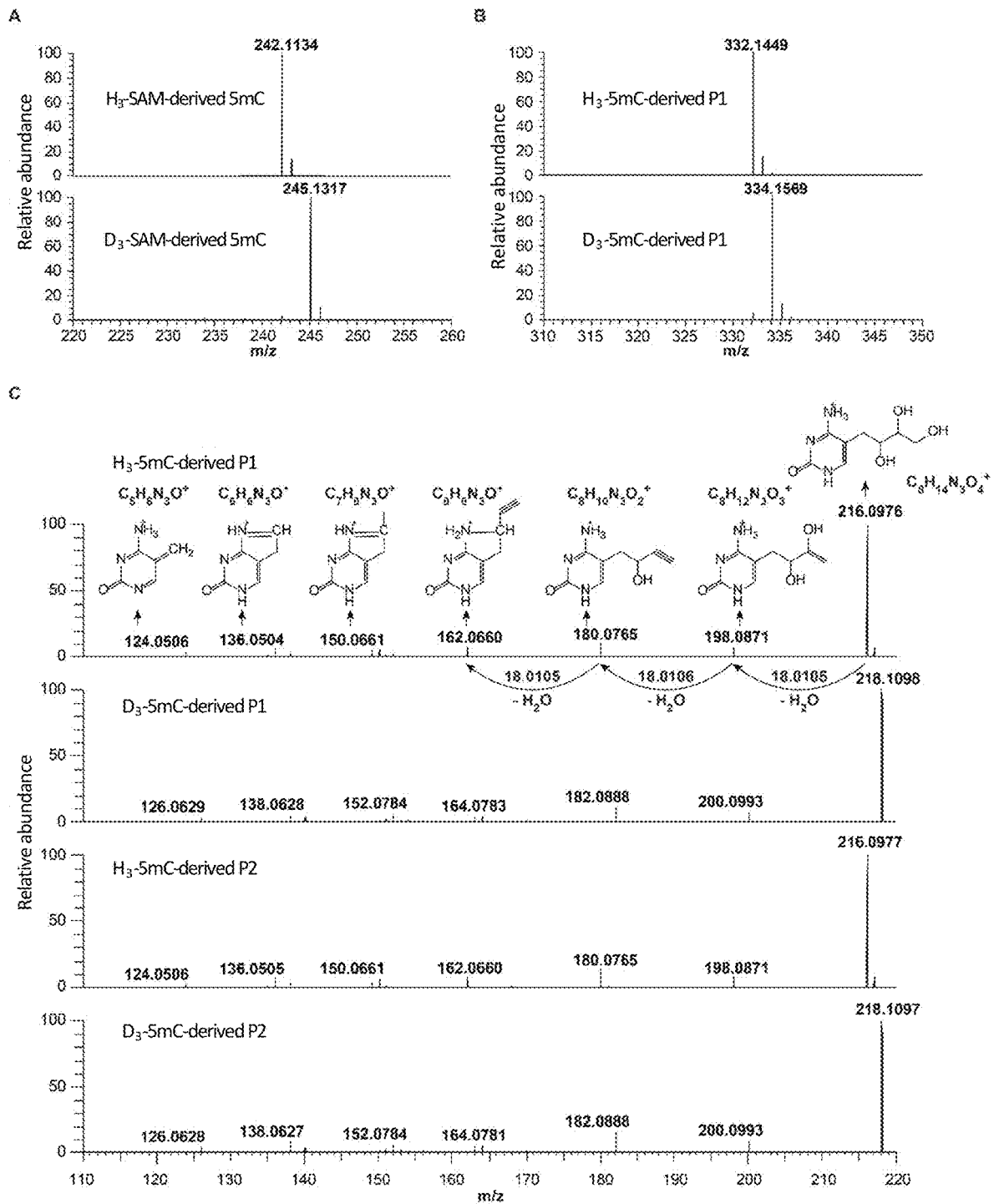

FIG. 5. Deuterium tracing experiments show the orientation of hydrogen atoms on the 5mC methyl group after Cmd1 reaction.

A: Mass spectrometry detection of 5mC in which the methyl group was specifically labeled with deuterium (D) in the DNA substrate (D3-labeled 5mC). The DNA substrate was prepared in vitro by reaction of M.SssI and D3-labeled S-(5'-adenosyl)-L-methionine (SAM). The relative molecular mass of the deuterated 5mC nucleoside on the methyl group was increased by 3 units compared to that of the unlabeled.

B: Mass spectrometry detection of P1 produced by D3-labeled 5mC. The relative molecular mass of P1 produced by deuterated 5mC was increased by 2 units relative to the P1 nucleoside derived from the unlabeled 5mC.

C: Speculation of the structure of the P1/P2 base and its fragments based on the m/z ratio of various ions measured by tandem mass spectrometry. P1 and P2 produce collision-induced dissociation (CID) fragments of identical mass, suggesting that they are likely to be isomers. The picture shows some CID fragments with the highest abundance of P1/P2, and the corresponding molecular formula and structural formula are calculated according to the measured relative molecular mass. Since all fragment ions of P1 or P2 derived from D3-labeled 5mC are increased by 2 units compared to fragment ions of P1 or P2 derived from unlabeled 5mC, the new modification is most likely to occur on a 5mC methyl group; from the CID results, the methylene group attached to the pyrimidine ring did not change during the CID process. In the CID, a fragment with a mass drop of 18.01 three times in succession appear at P1/P2, suggesting that there are three hydroxyl groups on the P1 and P2 structures, and equivalently, three dehydration reactions (MW 18.0100) occurred during mass spectrometry.

Figure 6:
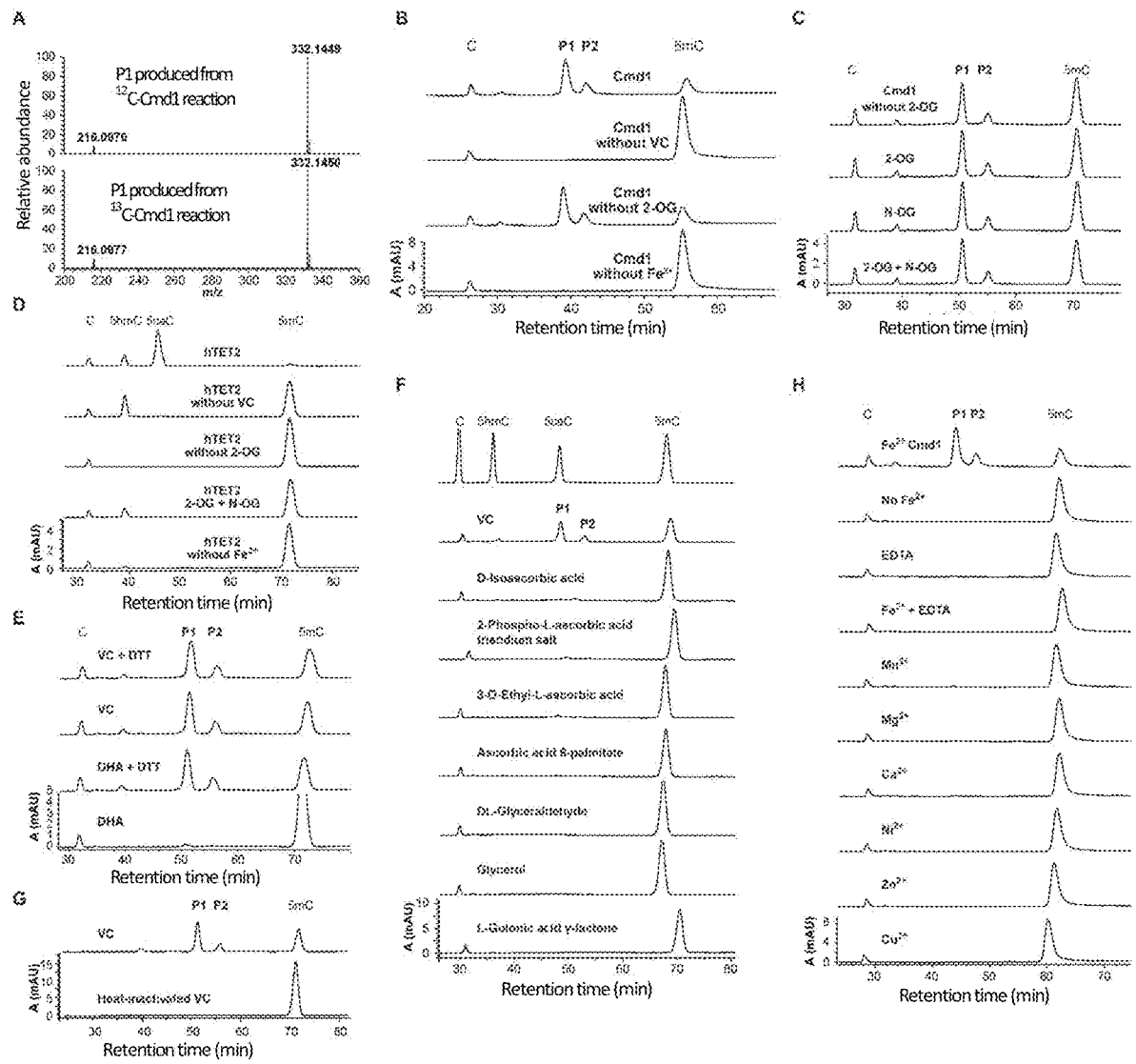

FIG. 6: Vitamin C (VC) is directly involved in the 5mC modification reaction. A: The 90 Dalton portion added to the P modification is not derived from Cmd1 or a compound co-purified with Cmd1. The Cmd1 protein used in this experiment was purified from *E. coli* grown in M9 minimal medium containing only $^{12}C$ or $^{13}C$-labeled glucose as the sole carbon source. The relative molecular mass of P1 produced by $^{13}C$-Cmd1 is not increased compared with P1 produced by $^{12}C$-Cmd1, which implies that the reactants required for the production of P1 are not derived from Cmd1 and co-purified compounds, but are derived from some component of an enzymatic activity reaction.

B: Dependence detection of Cmd1 enzymatic activity on each factor. The results of HPLC detection of Cmd1 after an enzymatic activity reaction under conditions where different small molecules are absent are indicated in the figure. VC is required in this reaction.

C: The enzymatic activity of Cmd1 is independent of 2-OG. The use of the 2-OG competitive inhibitor N-oxalylglycine (N-OG) did not affect the enzymatic activity of Cmd1.

D: 2-OG and $Fe^{2+}$ are essential for hTET2 enzymatic activity, while vitamin C is not required. The difference in enzymatic activity reaction conditions is shown in the annotation, and then the nucleoside composition in the DNA is detected by HPLC. N-OG is able to inhibit hTET2 activity.

E: The effect of oxidized VC and dehydroascorbic acid (DHA) on the enzymatic activity of Cmd1 was determined by HPLC. DHA can only support the enzymatic activity of Cmd1 after it has been reduced to VC by DTT.

F: HPLC detects the effect of various analogues of VC on the enzymatic activity of Cmd1.

G: HPLC detection of the effect of heat-inactivated VC on the enzymatic activity of Cmd1.

H: HPLC detection of the effect of $Fe^{2+}$ and other divalent metal ions on the enzymatic activity of Cmd1.

Figure 7:
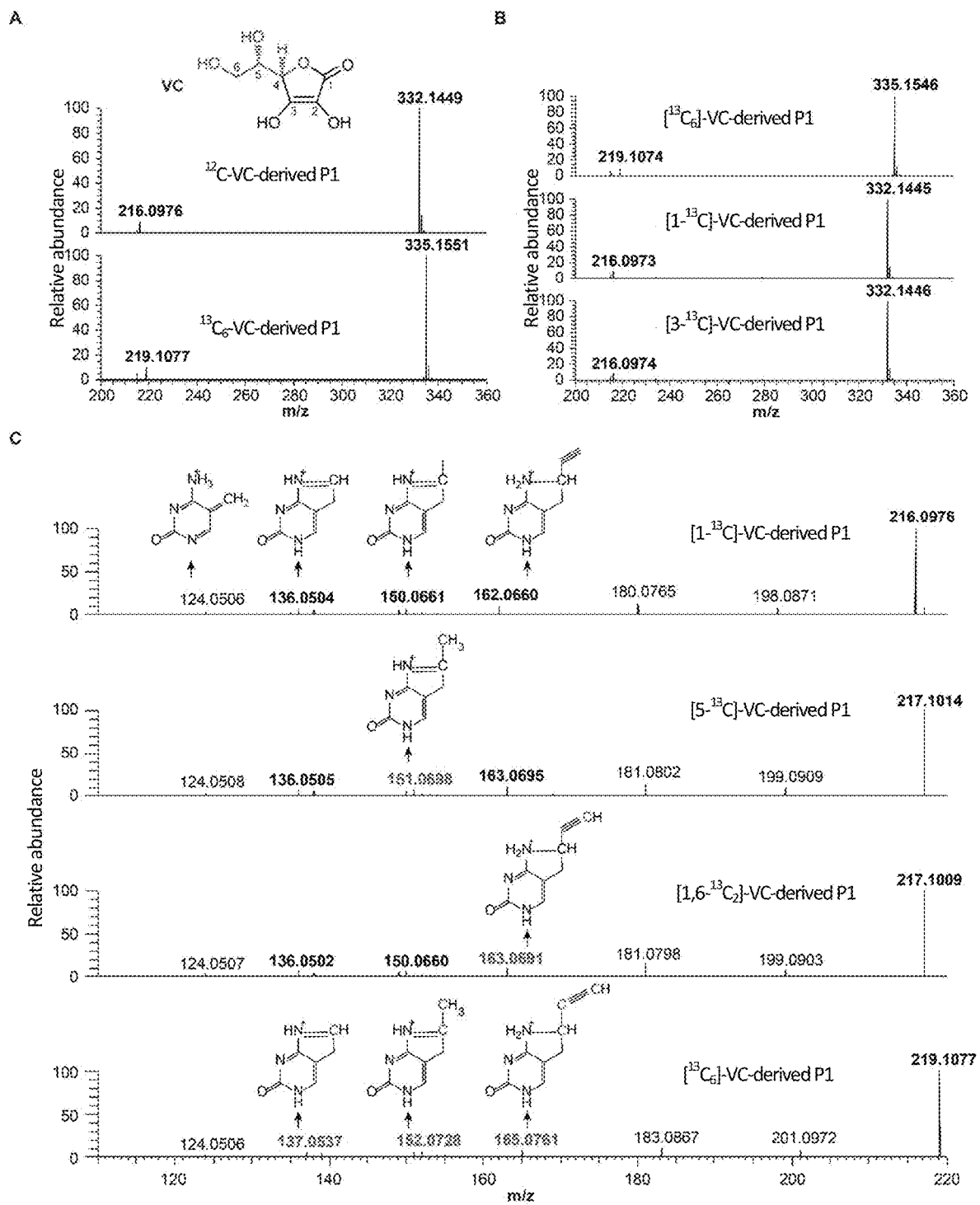

FIG. 7. VC is a glyceryl group donor in the process of Cmd1 catalyzing 5mC to produce new modifications.

A: VC is directly involved in the modification of 5mC. Mass spectrometry results show that the molecular weight of P1 produced by $^{13}C_6$-VC in replace of VC containing no isotope label was increased by 3 Daltons.

B: Mass spectrometry results show that $[1-^{13}C]$-VC and $[3-^{13}C]$-VC did not cause a change in the molecular weight of P1.

C: In the Cmd1 reaction, the C4-C6 portion of VC is transferred to the 5mC methyl group. When unlabeled VC is replaced with $[5-^{13}C]$-VC or $[1,6-^{13}C_2]$-VC, the molecular weight of the resulting P1 will be increased. The red label in the map shows the smallest molecular fragment containing $^{13}C$ atoms in P1 produced by VCs with different labels.

Figure 8:
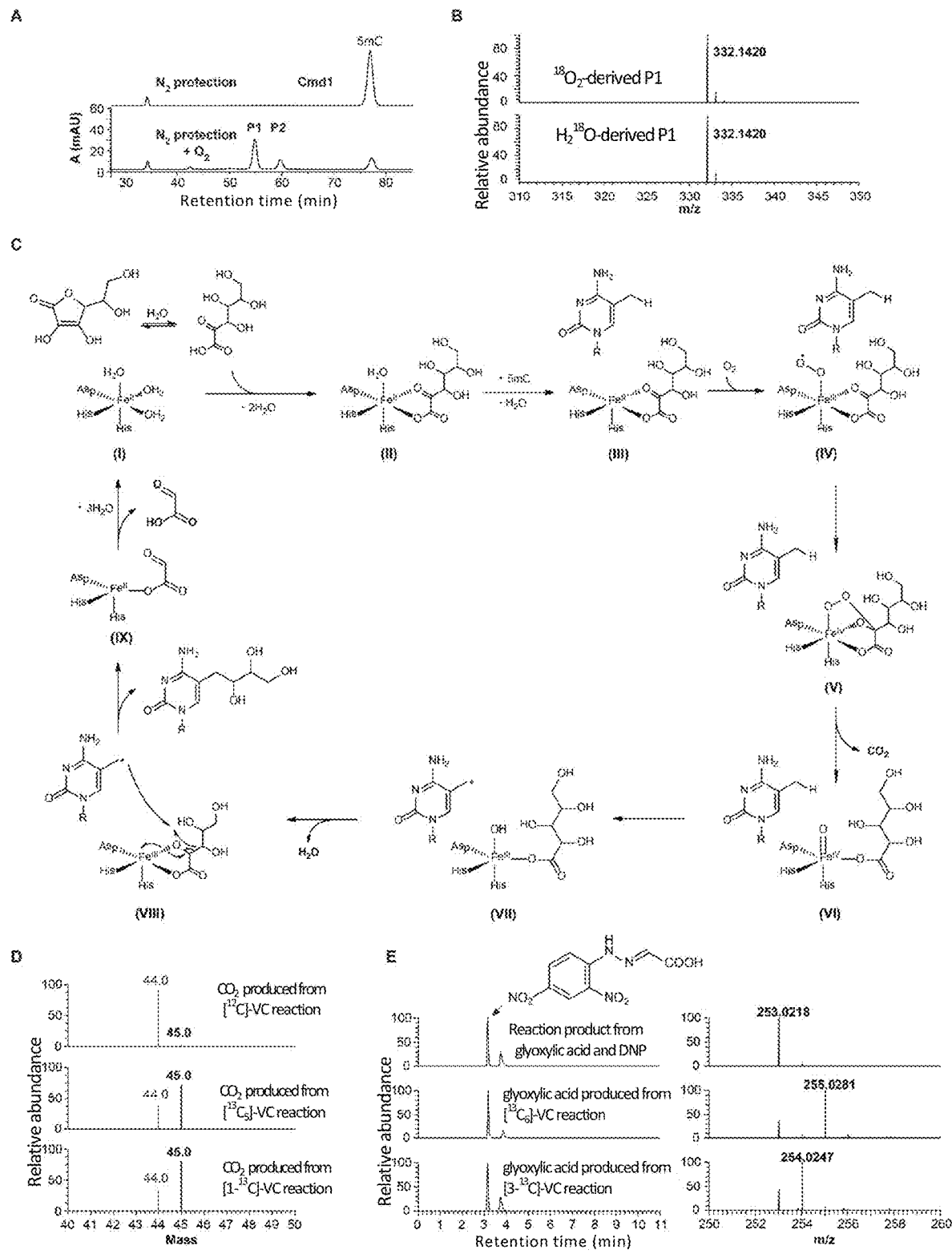

FIG. 8: Mechanism of VC involving in Cmd1 enzymatic activity reaction and detection of reaction products.

A: HPLC detection of the results of Cmd1 enzymatic activity reaction in an oxygen-free glove box. Experiments have shown that oxygen is indispensable for the enzymatic activity of Cmd1.

B: Mass spectrometry detection of the molecular weight of P1 produced by Cmd1 enzymatic activity reaction using $^{18}O$-labeled oxygen or water.

C: Prediction of the mechanism of Cmd1 enzymatic activity reaction. Firstly, Fe (II) coordinates with the His-X-Asp-Xn-His conserved domain on the Cmd1 protein, and the other three coordinate bonds are occupied by a water molecule (I). After the hydrolysis of VC, the carboxyl group on C-1 and the carbonyl group on C-2 are chelated with Fe (II) to replace two water molecules (II). When 5mC enters the vicinity of the enzymatic activity center of Cmd1, another water molecule on Fe (II) is detached (III). The combination of oxygen with the Fe (II) center produces the Fe (III)-superoxo superoxide intermediate (IV). The C-2-carbonyl group of the VC hydrolysate is subjected to nucleophilic attack by the distal oxygen of this intermediate, producing the Fe (IV)-peroxo peroxide group (V). The initial oxidative decarboxylation then produces a coordination intermediate (VI) of the Fe (IV)-oxo group with the carboxylic acid. This active group despoils a hydrogen atom from 5mC to form an Fe (III)-OH intermediate and a 5mC free radical (VII). The C-2-hydroxyl group on the coordination intermediate is chelated to the Fe (III) center, and the resulting water molecules are then detached from (VIII). The 5mC free radical attacks the coordination intermediate, causing homolysis of the C2-C3 carbon-carbon bond, and thus forming a P nucleoside and a glyoxylic acid (IX) bound to Fe (II). The glyoxylic acid then dissociates and Fe (II) returns to its original state and completes the entire reaction cycle.

D: Gas chromatography detection of the $CO_2$ released by $^{13}C$—VC.

E: Mass spectrometry detection of the glyoxylic acid produced by the Cmd1 reaction. Since glyoxylic acid has a low molecular weight and a large polarity, it is subjected to mass spectrometry after DNP derivatization.

Figure 9:
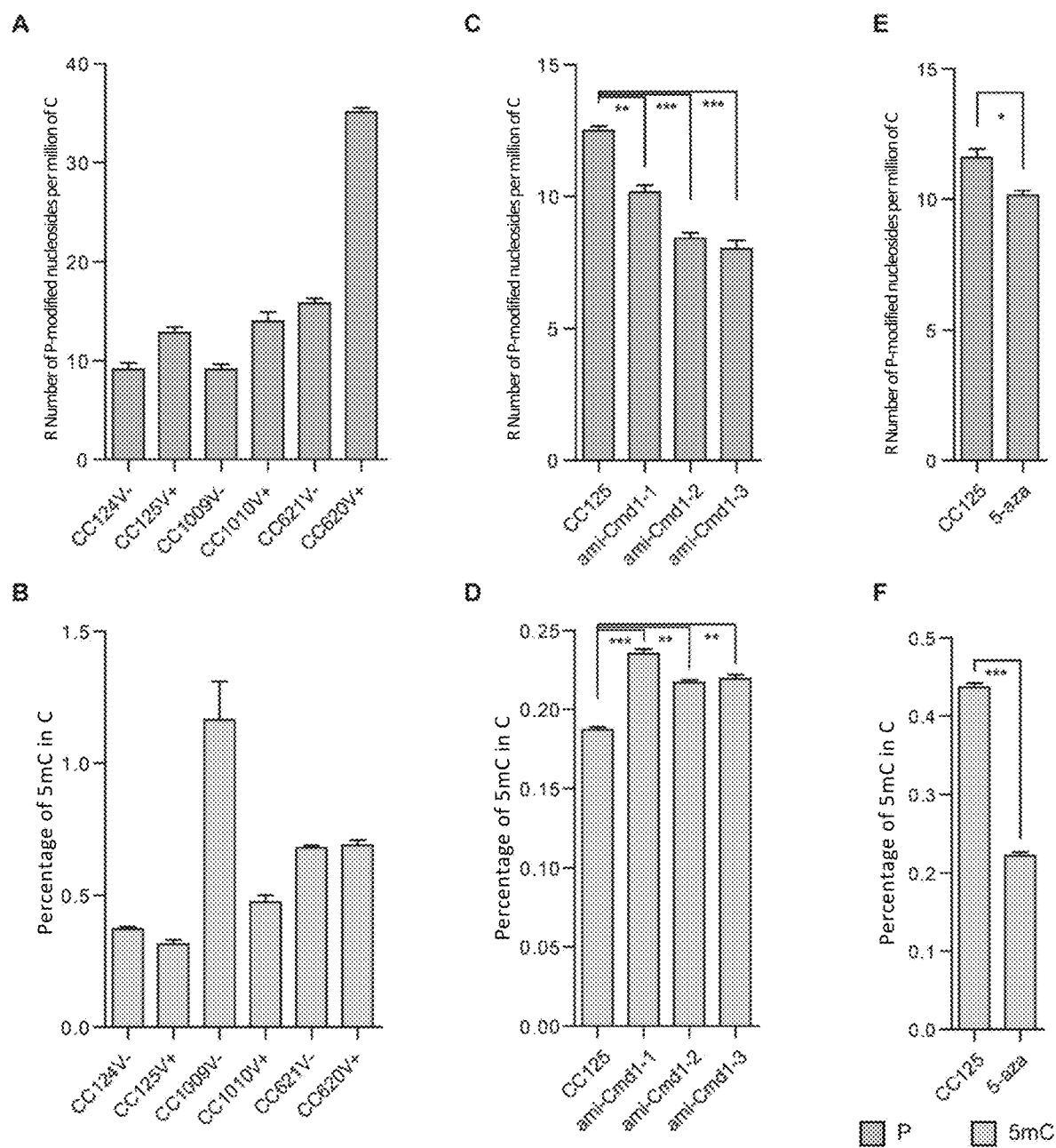

FIG. 9. P-modified bases are also present in CC125 *Chlamydomonas* strain cells, and their content varies depending on the expression level of Cmd1.

A/B: Triple quadrupole mass spectrometry detection of P modifications in genomic DNA and the content of 5mC. P represents the sum of P1 and P2 because P1 and P2 cannot be effectively distinguished under the conditions of this mass spectrometry experiment.

C/D: Detection of the P-modified bases and the content of 5mC in the Cmd1-knockdown strain. , $P<0.01$; *, $P<0.001$. The results suggest that the amount of Cmd1 enzyme is reduced, the resulting P modification is reduced, and the 5mC content is increased.

E/F: After treatment with 5-aza-2'-deoxycytidine (5-aza, a cytosine methyltransferase inhibitor), the level of 5mC and VC-derived P-modification in *Chlamydomonas* cells was significantly decreased. *, P<0.05; ***, P<0.001. In different 5-aza-treated cell lines, the level of expression of Cmd1 did not change.

Figure 10:
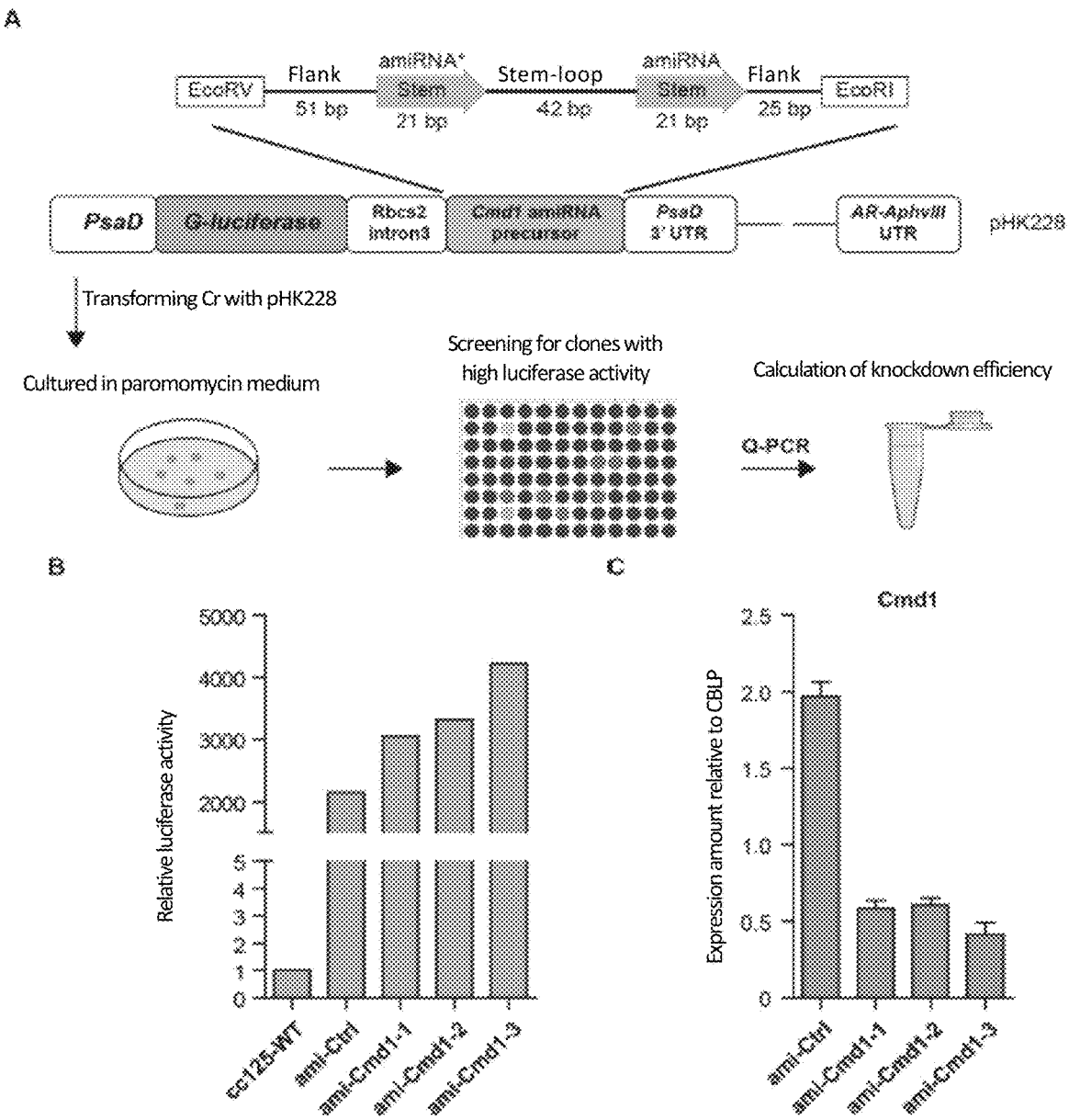

FIG. 10. Knockdown of Cmd1 in CC125 *Chlamydomonas* strain cells.

A: Construction of Cmd1 amiRNA recombinant plasmid and screening strategy for cell lines with high Cmd1-knockdown efficiency.

B: Relative luciferase activity assay of three knockdown cell lines (ami-Cmd1-1-3) and one control cell line (ami-Ctrl).

C: Relative expression levels of the Cmd1 gene in three knockdown cell lines (ami-Cmd1-1-3) and one control cell line (ami-Ctrl). The relative expression level of the Cmd1 gene was obtained by Q-PCR using the expression level of the CBLP gene as an internal reference. The average standard error from the experimental data of three independent replicates is shown in the figure.

Figure 11:
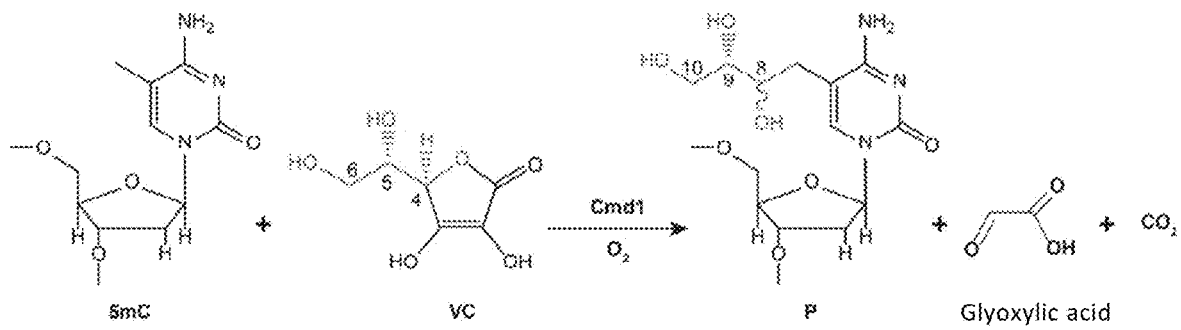

FIG. 11. Cmd1 catalytic reaction equation. In the Cmd1-catalyzed reaction, vitamin C, as a co-substrate, provides a glyceryl group that will be transferred to a methyl group of 5mC in DNA. In vitro, the glyceryl group and the 5mC-bonded carbon atom (C8) form two chiral isomers, P1 and P2, upon bonding. Glyoxylic acid and $CO_2$ are two by-products produced by the reaction of VC.

Figure 12:
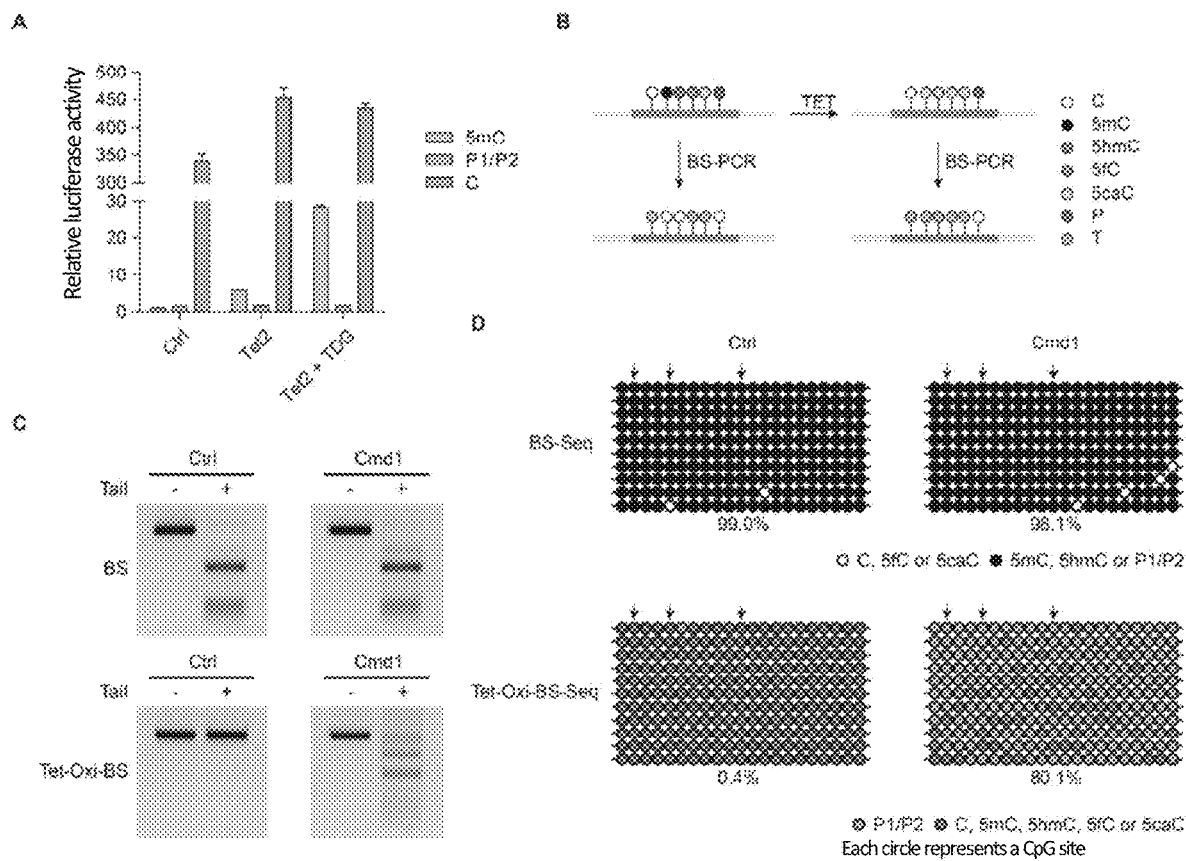

FIG. 12. 5mC new modification (P modification) produced by Cmd1 affects single-base level detection of gene expression and cytosine modification.

A: Reporter assay shows that P modification inhibited gene expression. In HEK293T cells, P modification on the promoter significantly affected the expression of the firefly reporter gene, and cotransformation of Tet2 and TDG also can not activate this reporter gene.

B: Schematic representation of the role of P modification in single-base detection against cytosine modification status based on Tet oxidation and bisulfite-seq (Tet-Oxi-BS-Seq). After combined bisulfite PCR (BS-PCR) amplification treatment, in Tet oxidation and DNA sequencing after bisulfite treatment, only P base was read in the form of "C".

C: COBRA (COmbined Bisulfite Restriction Analysis) data show that 5mC in DNA is protected from deamination by glycerol modification in vitro, and the form of C is maintained in the PCR amplification sequence, thereby being cleaved by TaiI restriction endonuclease (recognizing ACGT sequence).

D: Bisulfite-seq detection of P-modified bases produced by in vitro enzymatic activity. Each circle in the figure represents a CpG site. A small downward arrow indicates the TaiI cleavage site. Control (Ctrl) 5mC-DNA is present in Tet-Oxi-BS-Seq, 6.1% of which was read in C (orange), indicating that Tet oxidation or subsequent deamination conversion is incomplete. However, after 5mC-DNA was treated with Cmd1, a large portion of 5mC (about 80%) was protected.

Figure 13:
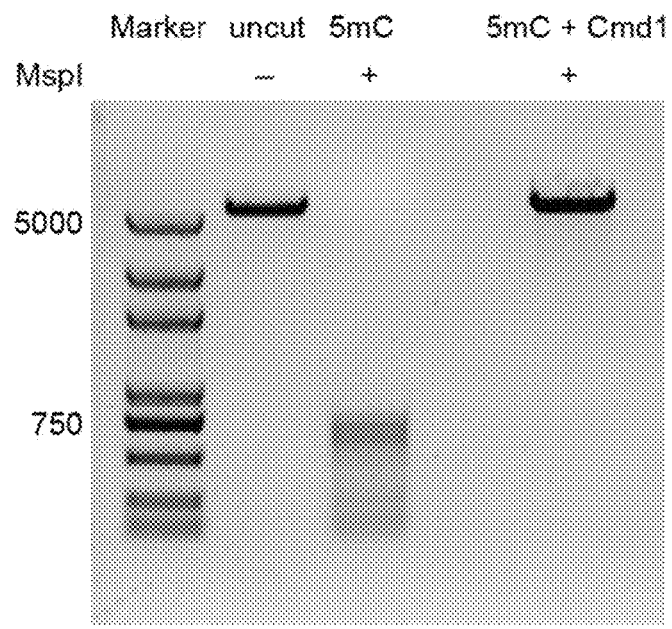

FIG. 13. Cmd1-mediated P modification affects the cleavage activity of the restriction endonuclease MspI (recognizing CCGG sequence) on 5mC-DNA.

DETAILED DESCRIPTION OF EMBODIMENTS 5-methylcytosine (5mC) is an epigenetic modification formed by methylation at the $5^{th}$ carbon atom of nucleic acid cytosine, and plays an important role in the growth and development of animals and plants and the occurrence and development of diseases. The present inventors have for the first time discovered a 5mC modifying enzyme (Cmd1) which can link a glyceryl group through a carbon-carbon single bond on a 5mC methyl carbon of a methylated nucleic acid. The present invention has been completed on this basis.

As used herein, unless otherwise stated, the "methylated nucleic acid" refers to a nucleic acid having a methylation modification at the $5^{th}$ carbon atom (C) on the cytosine of the nucleic acid strand. Nucleic acid methylation can cause changes in chromatin structure, nucleic acid conformation, nucleic acid stability, and the way nucleic acids interact with proteins, and changes in gene transcription (such as by silencing genes) to control gene expression.

As used herein, unless otherwise stated, the "Cmd1 enzyme" is *Chlamydomonas Tet*1. Preferably, the Cmd1 enzyme or a homologous protein thereof is present in the algae, including but not limited to *Chlamydomonas*, *Volvox*, etc.

As used herein, the nucleic acid includes: deoxyribonucleic acid (DNA) and ribonucleic acid (RNA).

The present invention discloses for the first time a method for adding a glyceryl group to a methyl group of 5-methylcytosine (5mC) of a methylated nucleic acid, comprising: treating a methylated nucleic acid with a Cmd1 enzyme, so that a glyceryl group is added to a methyl group of 5-methylcytosine (5mC) of the methylated nucleic acid. The method can be an in vivo method or an in vitro method.

The enzymatic activity of Cmd1 requires $Fe^{2+}$ as a cofactor, and vitamin C (VC), as an essential cofactor, directly participates in the Cmd1-catalyzed reaction and serves as a source of glycerol group donors.

The methylated nucleic acid is treated with the Cmd1 enzyme, thereby forming a product selected from the following:

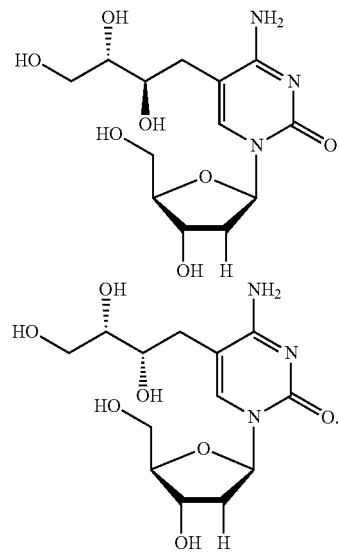

the present inventors have detected the presence of this new modification at both in vitro and in vivo levels. By reducing the expression level of the Cmd1 gene, the content of this modification is also reduced.

In the present invention, the Cmd1 enzyme may be naturally occurring, such as it may be isolated or purified from a mammal. Furthermore, the Cmd1 enzyme may also be artificially produced, for example, recombinant Cmd1 enzyme may be produced according to conventional genetic engineering recombination techniques. Preferably, a recombinant Cmd1 enzyme can be employed.

Cmd1 enzymes derived from other species are included in the present invention, particularly those having homology to the Cmd1 enzyme. Preferably, the corresponding Cmd1 enzyme sequence in the other species is more than 60%, more preferably more than 70%, more preferably more than 80%, more preferably more than 85%, more preferably more than 88%, more preferably more than 90%, more preferably more than 95%, more preferably more than 98% identical to the sequence of SEQ ID NO: 1 in the present invention.

Any suitable Cmd1 enzyme can be used in the present invention. The Cmd1 enzyme includes a full-length Cmd1 enzyme or a biologically active fragment thereof (also referred to as an active fragment).

Derivatives of the Cmd1 enzyme or biologically active fragments thereof formed by substitution, deletion or addition of one or more amino acid residues are also included in the present invention as long as they retain the function of the wild-type Cmd1 enzyme.

The Cmd1 enzyme or a biologically active fragment thereof includes a substitution sequence of part of conserved amino acids, which does not affect the activity thereof or retain a portion of the activity thereof. Proper replacement of amino acids is a technique well known in the art that can be readily implemented and ensures that the biological activity of the resulting molecule is not altered. These techniques have taught a person in the art that, in general, altering a single amino acid in a non-essential region of a polypeptide does not substantially alter biological activity. See Watson et al., Molecular Biology of The Gene, Fourth Edition, 1987, The Benjamin/Cummings Pub. Co. P224.

Any biologically active fragment of the Cmd1 enzyme can be used in the present invention. Here, the biologically active fragment of the Cmd1 enzyme means a polypeptide which still retains all or part of the function of the full-length Cmd1 enzyme. Typically, the biologically active fragment retains at least 50% of the activity of the full-length Cmd1 enzyme. Under more preferred conditions, the active fragment is capable of retaining 60%, 70%, 80%, 90%, 95%, 99%, or 100% of the activity of the full-length Cmd1 enzyme.

Once the sequence of the protein is obtained by isolation, the protein can be obtained in large quantities by recombination method. This method usually involves cloning coding genes into a vector, transforming it to a cell, and then obtaining the protein by isolating from the proliferated host cell by conventional methods. In addition, for shorter proteins, artificial synthesis (such as synthesis by a polypeptide synthesizer) can also be used to synthesize related sequences, and the artificial synthesis method can obtain the desired protein simply and quickly.

The present invention also encompasses an isolated nucleic acid encoding a biologically active fragment of the Cmd1 enzyme, or a complementary strand thereof. The DNA sequence encoding the biologically active fragment of the Cmd1 enzyme can be synthesized artificially in whole sequence or obtained by PCR amplification. After obtaining the DNA sequence encoding the biologically active fragment of the Cmd1 enzyme, it is ligated into a suitable expression vector and transferred to a suitable host cell. Finally, the desired protein is obtained by culturing the transformed host cells as well as by isolation and purification.

The present invention also encompasses vectors comprising a nucleic acid molecule encoding a biologically active fragment of the Cmd1 enzyme. The vector may further comprise an expression control sequence operatively linked to the sequence of the nucleic acid molecule to facilitate expression of the protein. By "operatively linked to" or "operably linked to" is meant a condition in which portions of a linear DNA sequence are capable of modulating or controlling the activity of other portions of the same linear DNA sequence. For example, if a promoter controls the transcription of a sequence, then it is operably linked to the coding sequence.

Furthermore, recombinant cells containing a biologically active fragment nucleic acid sequence encoding the Cmd1 enzyme are also included in the present invention. "Host cells" include prokaryotic cells and eukaryotic cells. Common prokaryotic host cells include E. coli, Bacillus subtilis, etc.; for example, E. coli cells, such as E. coli HMS174 (DE3), or BL21 (DE3). Common eukaryotic host cells include yeast cells, insect cells, and mammalian cells.

Based on the novel findings of the present inventors, the present invention provides the use of the Cmd1 enzyme or a biologically active fragment thereof, including but not limited to: the use for adding one glyceryl group to a methyl group of 5-methylcytosine of a methylated nucleic acid or for preparing a formulation for adding one glyceryl group to a methyl group of 5-methylcytosine of a methylated nucleic acid, etc.

As used herein, the up-regulator of the Cmd1 enzyme includes stabilizers, agonists, promoters, etc. Any substance which can increase the activity of the Cmd1 enzyme, maintain the stability of the Cmd1 enzyme, promote the expression of the Cmd1 enzyme, prolong the effective action time of the Cmd1 enzyme, promote transcription and translation of the gene of the Cmd1 enzyme can be used in the present invention as an effective substance that can be used to regulate (e.g., promote) glyceryl group modification on a methyl group of 5-methylcytosine of the methylated nucleic acids.

As used herein, the down-regulator of the Cmd1 enzyme includes an antagonist, an inhibitor, a retardant, a blocker, etc. Any substance which can reduce the activity of the Cmd1 enzyme, decrease the stability of the Cmd1 enzyme, inhibit the expression of the Cmd1 enzyme, shorten the effective action time of the Cmd1 enzyme, or inhibit transcription and translation of the gene of the Cmd1 enzyme can be used in the present invention as an effective substance that can be used to regulate (e.g., decrease) glyceryl group modification on a methyl group of 5-methylcytosine of the methylated nucleic acids.

Based on the novel findings of the present invention, and in conjunction with the common general knowledge, a person skilled in the art can prepare or design agonists or down-regulators of the Cmd1 enzyme, and such agonists or down-regulators are also included in the present invention.

As a preferred embodiment of the present invention, the up-regulator of the Cmd1 enzyme includes, but is not limited to, a plasmid expressing the Cmd1 enzyme.

The up-regulator of the Cmd1 enzyme can effect regulation of glyceryl group modification on the methyl group of 5-methylcytosine of the methylated nucleic acid by affecting the expression or activity of the Cmd1 enzyme or its coding gene.

The down-regulator of the Cmd1 enzyme may be a nucleic acid inhibitor, a protein inhibitor, an antibody, a ligand, a proteolytic enzyme, a protein-binding molecule, or EDTA, which is capable of down-regulating the expression or activity of the Cmd1 enzyme. As a preferred embodiment of the present invention, the down-regulator of the Cmd1 enzyme is a nucleic acid inhibitor designed based on the sequence of the gene encoding the Cmd1 enzyme, such as a small interfering molecule. The interfering RNA molecule can be delivered to the cells by the use of appropriate transfection reagents, or can be delivered to the cells using a variety of techniques known in the art. As a preferred embodiment of the invention, the interfering molecule is an artificial microRNA (amiRNA), and some preferred a miR-NAs are disclosed in the Embodiments. It is also a conventional technique in the art to screen antibodies (monoclonal antibodies or polyclonal antibodies) which inhibit protein activity according to known proteins.

The down-regulator of the Cmd1 enzyme achieves regulation of nucleic acid methylation by affecting the expression or activity of the Cmd1 enzyme.

As an embodiment, provided is the use of a Cmd1 enzyme down-regulator for reducing the level of a modified methylated nucleic acid which is a methylated nucleic acid carrying a glyceryl group on the methyl group of 5-methylcytosine.

The present invention discloses that Cmd1 mediates a novel epigenetic modification, and also points out a new fate determinant of 5mC and VC in this case. Since Cmd1 specifically modifies methylated nucleic acids, Cmd1-mediated modification can be used to prevent or promote further enzymatic or chemical modification: on the one hand, it can be used for the development of genetic engineering or gene therapy means based on changing gene function, and on the other hand, it can be used for the development of diagnostic techniques related to nucleic acid methylation profiling in vivo.

Based on the novel findings of the present invention, the present invention can be applied to the identification of the presence or amount of methylated nucleic acid, the method comprising: (1) treating the nucleic acid to be detected (e.g., genomic DNA) with a Cmd1 enzyme, thereby adding a glyceryl group to a methyl group of 5-methylcytosine of the methylated nucleic acid therein; and (2) identifying a product in which a glyceryl group modification occurs from the reaction product so as to determine the presence or amount of the methylated nucleic acid. An identifiable marker can be labeled on the glyceryl group donor for identification of 5-methylcytosine that produces this particular modification. In this method, vitamin C is also included as a glyceryl group donor in the reaction system, and a ferrous ion ($Fe^{2+}$) is present as a cofactor. An analogue of vitamin C having the same function as vitamin C is also included in the present invention as long as it also has a glycerol group which can be used as a donor. A person skilled in the art are aware of some well known vitamin C analogues including, but not limited to, dehydroascorbic acid, etc.

Based on the novel findings of the present invention, the present invention can be applied to a single-base detection method for detecting genetic modification on methylated nucleic acids. The method of bisulfite-seq (bisulfite sequencing) is now commonly used to detect the presence of 5mC on nucleic acids. In the traditional bisulfite-seq, C, 5fC and 5caC were deaminated to form U, which was read as T in PCR amplification; however, 5mC and 5hmC could not be deaminated, so they were still read as C after PCR amplification, thus being distinguished from C, etc. However, the traditional bisulfite-seq cannot distinguish between 5mC and 5hmC, and it is also impossible to distinguish C, 5fC and 5caC. Moreover, since the result of the P modification reading by bisulfite-seq is consistent with 5mC, it cannot be distinguished from 5mC. Therefore, the present inventors have proposed a combined Tet dioxygenase oxidation-bisulfite-seq method, that is, firstly, 5mC, 5hmC and 5fC are oxidized to 5caC by Tet dioxygenase, whereas the P modification cannot be oxidized by Tet, so that the 5mC and P modification can be distinguished by bisulfite-seq.

At the same time, in the absence of P modification in nucleic acids (such as gDNA), this method can also be used to distinguish between 5mC and 5hmC. First, the nucleic acid was treated with Cmd1, and all 5mC was converted to P modification, whereas 5hmC stayed the same. Further, a combined Tet dioxygenase oxidation-bisulfite-seq method was used to distinguish 5mC from 5hmC.

It is clear that the new product produced by the reaction of 5mC with VC catalyzed by Cmd1 can be used in the latest nucleic acid sequencing to detect the content of 5mC.

The technical scheme of the present invention combines the third-generation or updated nucleic acid sequencing technique, including but not limited to SMRT sequencing and nanopore sequencing, etc., which can directly distinguish 5mC form 5mC modified by a glycerol group, thereby achieving the purpose of single-base determination of 5mC modified by a glycerol group. At present, the third-generation sequencing technique is temporarily unable to distinguish between 5mC and C, but can distinguish C from 5hmC, 5fC and 5caC; therefore, based on the third-generation or updated sequencing technique, Cmd1 treatment is used to specifically identify 5mC, thus achieving the purpose that C, 5mC, 5hmC, 5fC, and 5caC were simultaneously distinguished.

In addition, a Cmd1 protein can be used to detect the presence of VC. Since VC is essential and irreplaceable in this reaction, the Cmd1 protein and 5mC-nucleic acid can be used to detect the presence of VC with high sensitivity and specificity.

The method of the present invention, combined with next generation nucleic acid sequencing (third-generation or updated sequencing) technique, enables simultaneous determination of sequences and modifications.

The methods of the present invention also provide a new avenue for site-directed alteration of the structure of nucleic acid fragments or genes, and can also play a role in a variety of DNA nanotechnology. The method of the present invention can also be applied to the extension of carbon chains in organic synthesis and the synthesis of compounds containing a glycerol group.

Based on the novel findings of the present invention, also provided is a method of targeted regulation of gene expression, the method comprising: based on that Cmd1-mediated new 5mC modification can significantly inhibit gene expression, Cmd1 can be used in combination with gene targeting elements; preferably, the targeted regulation of gene expression can be achieved by binding the Cmd1 enzyme to CRISPR-Cas9 or TALEN, and can be used for targeted regulation of oncogenes, etc. to achieve treatment. In addition, combined use of CRISPR-Cas9 or TALEN with Cmd1 can also be used to reduce the level of 5mC modification of the target gene.

Based on the novel findings of the present invention, there is also provided a method for altering the effects on protein binding or enzymatic activity on the endogenous genome or in vitro DNA of a cell. The Cmd1-mediated 5mC modified by a glycerol group altered the original properties of the 5mC, which affected its binding to proteins. For example, after Cmd1 modification, it can be used to alter the enzymatic activity of a restriction endonuclease such as MspI, etc.

Based on the novel findings of the present invention, there is also provided a kit (or a pill case) for adding a glyceryl group to a methyl group of 5-methylcytosine of a methylated nucleic acid, including: Cmd1 enzyme or its up-regulator. More preferably, the kit further comprises: a Cmd1 enzyme or its up-regulator; vitamin C; and a ferrous ion or a substance capable of forming a ferrous ion. The kit integrates reagents into a kit for their commercial application.

As a preferred embodiment of the present invention, other reagents such as reagents for quantitatively or qualitatively analyzing the methylation status of the nucleic acid, etc. may be included in the kit. More preferably, the kit may also include instructions for use in order to facilitate use.

The present invention is further illustrated below in conjunction with specific embodiments. It is to be understood that these examples serve only to illustrate the present invention and are not limiting the scope of the present invention. In the following embodiments, experimental methods without specifying specific conditions are generally performed under conventional conditions (such as those described in J. Sambrook et al., Guide to Molecular Cloning, Third Edition, Science Press, 2002) or following the manufacturer's recommended conditions.

Materials and Methods

1. Expression and Purification of Cmd1 Recombinant Protein

The present inventors cloned the coding sequence of the Cmd1 gene into the transformed pET28a expression vector (pPEI-His-Sumo, obtained from Xu Yanhui Laboratory of Fudan University), and expressed same in *E. coli* BL21 (DE3).

The coding sequence of the Cmd1 mutant was also cloned into the same expression vector. The Cmd1 amino acid sequence is, for example, SEQ ID NO: 1; based on the sequence, the Cmd1 mutant has an A330V mutation, a H345A mutation, a D347A mutation, a D350A mutation, a H345Y and D347A (H345Y/D347A) mutation, respectively. The recombinant expression vector was transformed into *E. coli* BL21 (DE3) for inducible expression.

When *E. coli* was cultured to an OD600 of 0.8, isopropyl-β-D-thiogalactoside (IPTG) at a final concentration of 0.1 mM was added and induced at 16° C. for 16 h. The His-Sumo-labeled Cmd1 fusion protein in the protein extract was first bound to Ni-NTA purification reagent (Qiagen), and then incubated with His-UlpI protease at 4° C. overnight to excise the His-Sumo label in the fusion protein. The enzyme digestion solution was collected and purified using a Resource 15 Q anion exchange column (GE Healthcare), and eluted at a linear gradient from 100/0 to 50/50 with buffer A (20 mM Tris-HCl, pH 8.5)/buffer B (20 mM Tris-HCl, pH 8.5, 1 M NaCl). The eluate was further purified by gel filtration chromatography using a Superdex 200 10/300 GL gel column (GE Healthcare) and buffer C (20 mM HEPES pH 7.0, 100 mM NaCl), respectively. The eluate from the gel filtration chromatography was concentrated using an Ultracel-10K ultrafiltration tube (Millipore) to a protein concentration of 10 μg/l.

2. Preparation of DNA Substrate Required for In Vitro Enzymatic Activity of Cmd1

Taking *Chlamydomonas reinhardtii* genomic DNA as a template, replacing conventional dCTP with 5m-dCTP, a 1.1 kb 5mC-DNA fragment was amplified by PCR. To test the specificity of Cmd1 for the reaction substrate, 5hm-dCTP as well as unmodified dCTP were also used to obtain similar products by PCR amplification. The upstream and downstream primers used in PCR are:

5'-biotin-AAGGGTTGGATTGTAGGTAGTT-TAGAAAT-3' (SEQ ID NO: 11), and
5'-TGAGGGTGGTAAATTAG-3' (SEQ ID NO:12).

3. In Vitro Enzymatic Activity Assay of Cmd1

In a 100 μl reaction system, 0.5 μg of biotin-labeled 5mC-DNA substrate and 4 μg of Cmd1 enzyme (a molar ratio of enzyme to 5mC of about 1:2) were reacted in a system containing 50 mM HEPES (pH 7.0), 50 mM NaCl, 1 mM L-ascorbic acid, 1 mM ATP, 1 mM DTT and 0.1 mM $Fe(NH_4)_2(SO_4)_2$ at 37° C. for 1 h. In the $^{13}C$ tracer experiment, $^{13}C$-labeled L-ascorbic acid was purchased from Omicron Biochemicals. After the reaction was completed, proteinase K was added to the reaction system to digest the protein, and the biotin-labeled DNA was then purified by Streptavidin Sepharose purification reagent (GE Healthcare), and please refer to the instruction manual for the specific process.

4. High Performance Liquid Chromatography (HPLC) Detection of the Nucleoside Composition of DNA Substrate after Cmd1 Reaction The HPLC detection comprises the following steps: the purified biotin-labeled DNA substrate was digested with nuclease P1 (Sigma) in a system containing 0.2 mM $ZnSO_4$ and 20 mM NaAc (pH 5.3) for at least 1 h at 55° C., CIAP (Takara) and its buffer were then added and reacted at 37° C. for 1 h to remove the phosphate group. After centrifugation, the supernatant of the sample was taken for HPLC analysis. The instrument used was Agilent 1260 and the analytical column was Welch AQ-C18 column (4.6×250 mm, 5 m). The mobile phase used to detect the nucleoside composition was 10 mM $KH_2PO_4$ (pH 3.85) at a flow rate of 0.6 ml/min and a temperature of 15° C. The mobile phase used to recover the P-modified nucleoside was 20 mM $NH_4Ac$ (pH 5.21) at a flow rate of 1 ml/min and a temperature of 15° C. The detection wavelength is 280 nm.

5. Preparation of 5mC-DNA Containing a $^{14}C$- or Deuterium (D)-Labeled Methyl Group In a 100 μl reaction system containing 8 μl of S-[methyl-$^{14}C$]-L-methionine ($^{14}C$-SAM, 1.48-2.22 GBq/mmol, PerkinElmer) or S-[methyl-$D_3$]-adenosyl-L-methionine ($D_3$-SAM, Zzstandard), 5 μg of plasmid DNA and 20 units of M.SssI CpG methyltransferase (Zymo Research) were incubated overnight at 30° C. The labeled DNA after the reaction was purified and recovered using Qiaquick Nucleotide Removal Kit (Qiagen).

6. Thin Layer Chromatography (TLC) Detection of 5mC Derivatives

The $^{14}C$-5mC-DNA-containing substrate was incubated with Cmd1, and after digestion with proteinase K, the DNA was purified by extraction with phenol chloroform and ethanol. The DNA pellet was dissolved in 8 μl of water, lysed with nuclease P1, and 0.5 μl of the lysate was spotted on a PEI-cellulose TLC plate (Merck). The TLC plate with the sample was developed with isopropanol:HCl:$H_2O$ (70:15:15), finally compressed using a phosphor screen, and scanned on a FujiFilm Fluorescent Image Analyzer FLA-3000.

7. Determination of P Modification Content in *Chlamydomonas* Genome by Liquid Chromatography-Mass Spectrometry (LC-MS)

In order to accurately determine the molecular weights of the two derivatives produced by 5mC with catalysis by Cmd1, the present inventors separated the two derivatives by HPLC, followed by analysis and determination by UPLC-MS/MS. The instrument and analytical column used by the present inventors are a Q Exactive mass spectrometer (Thermo Scientific) and an ACQUITY UPLC HSS T3 analytical column (1.8 m) respectively, buffer A (0.05% $CH_3COOH$) and buffer B (acetonitrile, ACN) are used as a mobile phase, and the analysis was carried out at a flow rate of 0.3 ml/min. For the analysis, buffers A and B were mixed according to the following gradient: starting at a condition of 100% A, adjusted to 95% A at a linear gradient over 0-2 mins, reduced to 50% A at a linear gradient over 2-4 mins, and running for 1 min at this mixing ratio, then reduced to 0% A over 0.1 min, adjusted back to the starting condition at 8 mins, and equilibrated for 1 min.

The present inventors used MRM (multiple reaction monitoring)-based LC-MS/MS to detect the content of P modification in Chlamydomonas genomic DNA. The mass spectrum was completed using a UPLC system (1290 series, Agilent Technologies) coupled to a triple quadrupole mass spectrometer (Agilent 6495 QQQ, Agilent Technologies). The analytical column used was ACQUITY UPLC BEH amide column (1.7 m, 2.1 mm×100 mm, Waters). The buffer used was buffer A (25 mM ammonium acetate, 25 mM ammonia) and buffer B (acetonitrile), and the analysis was carried out at a flow rate of 0.6 ml/min. For the analysis, buffers A and B were mixed according to the following gradient: starting at a condition of 85% B, reduced to 40% B at a linear gradient over 0-2 mins, and running for 2 mins at this mixing ratio, then reduced to the starting condition of B over 0.1 min and equilibrated for 3 mins at this mixing ratio. Assay parameters for detection of three nucleosides P, 5mC and C in genomic DNA samples were optimized according to the standards of the three nucleosides, P: 332.1/216.1 (quantifier transition, CE 24) and 332.1/150.0 (qualifier transition, CE 44); 5mC: 242.1/126.1 (quantifier transition, CE 8) and 242.1/54.3 (qualifier transition, CE 60) and C: 228.1/112.1 (quantifier transition, CE 8) and 228.1/41.3 (qualifier transition, CE 64); G: 268.1/152.1 (quantifier transition, CE 21); 268.1/135 (quantifier transition, CE 45). All compounds were tested in cationic ESI mode. Under the above detection conditions, the retention times of P, 5mC and C were 1.50 mins, 1.06 mins and 1.12 mins, respectively. The amount of each nucleoside is calculated based on its peak area which was measured under a particular ion pair transition (P: 332.1/216.1, 5mC: 242.1/126.1 and C: 228.1/112.1, G: 268.1/152.1) and substituted into a standard curve.

8. Nuclear Magnetic Resonance (NMR) Analysis of P-Modified Nucleoside Structure

Purified P1 and P2 were dissolved in phosphate buffer (0.1 M, solvent $D_2O$, pD 7.4), respectively, and the corresponding NMR data were acquired by a Bruker 600 MHz and 850 MHz spectrometer equipped with a 5-mm cryogenic TCI probe. According to previous literature reports (H. Liu et al., Identification of Three Novel Polyphenolic Compounds, Origanine A-C, with Unique Skeleton from *Origanum vulgare* L. Using the Hyphenated LC-DAD-SPE-NMR/MS Methods. *J Agric Food Chem* 60, 129-135 (2012)), the present inventors collected one-dimensional $^1H$ NMR spectra and a series of two-dimensional (2D) NMR spectral data including $^1H$-$^1H$ COSY, $^1H$-$^1H$ TOCSY, $^1H$ JRES, $^1H$-$^{13}C$ HSQC and $^1H$-$^{13}C$ HMBC 2D spectra. The methyl signal of TSP ($\delta_H$ 0.000, $\delta_C$ 0.00) was taken as a reference for the chemical shift signals of $^1H$ and $^{13}C$.

The three-bond coupling constant J ($^3J$) is calculated from the protons on the chiral carbon atoms (C8 and C9) on the side chain and their adjacent carbon atoms (C7 and C10). For P1 and P2, three-bond coupling constant J of four possible configurations (8R,9R, 8S,9S, 8R,9S, 8S,9R) can be calculated based on the molecular geometry density functional theory (DFT) optimized at wb97xd/6-311G (d, p) level. All results were calculated using the Gaussian 09 software package based on Ramsey theory (M. J. Frisch et al. (Gaussian, Inc., Wallingford, CT, USA, 2009)), considering Fermi contact, diamagnetic spin orbit, paramagnetic spin orbit and rotation-dipole.

9. *Chlamydomonas reinhardtii* Strain and Culture Method

The wild type *Chlamydomonas* strains (CC124/125, CC1009/CC1010, CC620/CC621) were obtained from the *Chlamydomonas* Genetic Center. All *Chlamydomonas* strains were cultured with shaking in Tris/acetate/phosphate (TAP) medium at 25° C. with a light intensity of 50 $\mu mol \cdot m^{-2} \cdot s^{-1}$.

In the 5-aza-2'-deoxycytidine (5-aza, Sigma) treatment experiment, the present inventors used CC125 *Chlamydomonas* strain with an initial cell concentration of 1.2× $10^4$ ml-1 and cultured same in TAP medium containing 400 µM 5-aza. The TAP medium containing the newly formulated 5-aza was replaced on the next day, and the cells were harvested on the fourth day and used for subsequent experiments.

10. Use of Artificial microRNA (amiRNA) to Reduce Cmd1 Expression in *Chlamydomonas reinhardtii*

The design and construction strategy of Cmd1 amiRNA is based on the report of Hu et al. in 2014 (J. Hu, X. Deng, N. Shao, G. Wang, K. Huang, Rapid Construction and Screening of Artificial microRNA Systems in *Chlamydomonas reinhardtii*. Plant J 79, 1052-1064 (2014)). The present inventors designed eight short oligonucleotide strands (Table 1) for assembly to produce a Cmd1 amiRNA precursor (the precursor sequence is: atcaggaaac-caaggcgcgctagcttcctgggcgcagtgttccagctgcagtacGGGGTC CTTATTCAAGGCATAtctcgctgatcggcaccatgggggtggtggt-gatcagcgctaTATGGCTTG AATAAGGACCCCtactgcagccg-gaacactgccaggagaatt (SEQ ID NO:10)). The VIPP1 amiRNA precursor on the pHK226 vector (J. Hu et al.) was then replaced with this precursor, and the resulting new plasmid was named as pHK227. The third intron of the RBCS2 gene was amplified from the *Chlamydomonas* genome (GenBank accession number NW_001843932.1, at position 37072-37301) and inserted into pHK227 after digestion with EcoRV, and the newly constructed plasmid was named as pHK228. Plasmid pHK228 was linearized with SacI and electroporated into CC125 *Chlamydomonas* strain cells using Bio-Rad Gene Pulser II (K. Shimogawara, S. Fujiwara, A. Grossman, H. Usuda, High-efficiency Transformation of *Chlamydomonas reinhardtii* by Electroporation. *Genetics* 148, 1821-1828 (1998)). Paromomycin resistant clones were picked and cultured in clear 96-well plates and the level of luciferase expression in each clone was determined.

TABLE 1

Synthesis of amiRNA precursor sequences targeting Cmd1

| | |
|---|---|
| mir1157-uni-1F | 5'-atcaggaaaccaaggcgcgctagct-3' (SEQ ID NO: 2) |
| mir1157-uni-2R | 5'-gtactgcagctggaacactgcgcccag gaagctagcgcgccttggtttcctgat-3' (SEQ ID NO: 3) |
| mir1157-Cmd1-3F | 5'-tcctgggcgcagtgttccagctgcagt acGGGGTCCTTATTCAAGGCATA-3' (SEQ ID NO: 4) |
| mir1157-Cmd1-4R | 5'-ccatggtgccgatcagcgagaTATGCC TTGAATAAGGACCCC-3' (SEQ ID NO: 5) |
| mir1157-uni-5F | 5'-tctcgctgatcggcaccatgggggtgg tggtgatcagcgcta-3' (SEQ ID NO: 6) |

TABLE 1-continued

Synthesis of amiRNA precursor sequences targeting Cmd1

| | |
|---|---|
| mir1157-Cmd1-6R | 5'-GGGGTCCTTATTCAAGCCATAtagcgc tgatcaccaccaccc-3' (SEQ ID NO: 7) |
| mir1157-Cmd1-7F | 5'-TATGGCTTGAATAAGGACCCCtactgc agccggaacactgccaggag-3' (SEQ ID NO: 8) |
| mir1157-uni-8R | 5'-aattctcctggcagtgttccggctgca gta-3' (SEQ ID NO: 9) |

In order to further determine the expression level of Cmd1 in cells, the present inventors used qPCR (quantitative PCR) to measure the transcription level of Cmd1 mRNA in the above-mentioned selected cell clone with high luciferase activity, the instrument used was CFXP6™ Real-Time PCR instrument, and the reagent used is SYBR Premix™ Ex Taq (Tli RNaseH Plus, Takara). The Cmd1 cDNA fragment was amplified using the primers Cmd1-qF (5'-CCACAAACAT-CATCTCTCTCACC-3'(SEQ ID NO:13)) and Cmd1-qR (5'-AT GGTGAAGTCCAGTGGTTGA-3'(SEQ ID NO:14)), and Cblp (G-protein beta subunit-like polypeptide) cDNA fragment was amplified using primers Cblp-qF (5'-GT-CATCCACTGCCTGTGCTT-3'(SEQ ID NO:15)) and Cblp-qR (5'-CCTTCTTGCTGGTGATGTTG-3'(SEQ ID NO:16)). Cblp was used as an internal reference in this experiment.

11. Large-Scale Preparation of Genomic DNA from *Chlamydomonas reinhardtii*

CTAB was used to extract genomic DNA from *Chlamydomonas reinhardtii* and was dissolved in nuclease-free water for subsequent experiments.

12. Statistical Analysis

All experimental data were average standard errors calculated by three independent replicate experiments. The statistical differences of each group of data were evaluated using the two-tailed test in GraphPad software. When P<0.05, it is considered that there is a significant difference.

Embodiment 1. Formation of two new modifications by Cmd1 catalyzing 5mC In order to study the enzymatic activity of the *Chlamydomonas* Tet homologous protein CrTet, the present inventors expressed and purified these proteins from *Escherichia coli* and performed in vitro enzyme activity analysis. The Coomassie blue staining image of the unlabeled Cmd1 purified from *E. coli* is shown in FIG. 2A; the Coomassie blue staining image of the Cmd1 mutant is shown in FIG. 3A.

Unexpectedly, after the CrTet1 enzymatic activity test with 5mC-DNA as a substrate, the HPLC results showed that two peaks (P1/P2) with completely different retention times from the nucleoside standards formed, whereas when the mutant protein (Mut Cmd1, H345/D347) of the conserved site of CrTet1 was used for testing, the corresponding peak could not be detected; at the same time, 5mC-DNA reacted with Cmd1, and the accumulation of P1/P2 content was consistent with the decrease of 5mC with time, as shown in FIGS. 2B-D and FIGS. 3A-B.

However, the present inventors were unable to detect the accumulation of P1/P2 when using 5hmC-DNA and C-DNA (referring to conventional unmodified DNA) as a substrate, indicating that this reaction is likely to use 5mC as a direct substrate, as shown in FIG. 3C.

To further determine the results of HPLC, the present inventors labeled the methyl carbon atoms of 5mC-DNA with a $^{14}$C radioisotope and used in thin layer chromatography (TLC) experiments. Using this isotope-labeled 5mC-DNA as a substrate, after reacting with wild-type Cmd1, the present inventors also observed a site where two unknown products are formed on the chromatographic plate, whereas the mutant Cmd1 at some conserved amino acid sites does not have this function, as shown in FIG. 2E.

All of the above experiments show that the present inventors have discovered a new 5mC-modifying enzyme (Cmd1) which can catalyze 5mC to form two new modifications. In addition, based on experimental results and the results of sequence alignment, it is suggested that H345 and D347 are sites that bind to a ferrous ion, A330 is the center site of the enzymatic activity of Cmd1, and D350 interacts with 5mC. That is, A330, H345, D347 and D350 are key sites for the enzymatic activity of Cmd1. Cmd1 has more than 500 amino acids, and other amino acids at some non-conserved sites other than A330, H345, D347 and D350 at the conserved sites may be replaced by similar amino acids.

Embodiment 2. Analysis of the Structure of the Two New Products P1 and P2

In order to analyze the structures of the two new products found in Embodiment 1, the present inventors performed the high resolution mass spectrometry analysis of the separated reaction products.

Mass spectrometry results show that in the positive ion mode, mass to charge ratios of P1 and P2 are 332.1448 and 332.1449, respectively, so as to infer that the molecular formulae of P1/P2 are the same, $C_{13}H_{21}N_3O_7$, as shown in FIG. 4A.

Since the fragment ion spectra of P1 and P2 are exactly the same, presumably P1 and P2 belong to stereoisomers, as shown in FIG. 5C.

To determine whether the additional molecular weight of 90 Daltons of P1 and P2 over 5mC was directly added to the methyl group, deuterated 5mC-DNA was used for the Cmd1 enzymatic activity experiment. Compared to unlabeled 5mC, the molecular weight of the deuterated 5mC was increased by 3, as shown in FIG. 5A. The molecular weight of P1/P2 produced by the Cmd1 reaction using deuterated 5mC was only increased by 2 compared with the unlabeled, as shown in FIG. 5B. This indicates that one hydrogen atom on the methyl group of 5mC is substituted in the enzymatic reaction of Cmd1, and the remaining methylene groups are retained in the fragments of the secondary mass spectrum. By careful analysis of molecular fragments of secondary mass spectrometry, the present inventors have discovered that P1/P2 ions continuously lose three water molecules after neutral loss of one deoxyribose, suggesting that there may be three hydroxyl groups in the molecular structure of P1/P2, as shown in FIG. 5C.

In order to determine the molecular structure of P1/P2, the present inventors conducted nuclear magnetic resonance experiments and density functional theory calculations. The two-dimensional nuclear magnetic resonance spectrum clearly gives the planar molecular structure of P1/P2. Taking P1 as an example, the peaks of COSY and TOCSY confirmed the presence of a trihydroxybutyl group, —CH$_2$CH (OH)CH(OH)CH$_2$OH. In addition, the HSQC and HMBC spectra further confirmed the connection between different atoms, and confirmed that the structural formula of P1 is: 5-(1-[2,3,4-trihydroxybutyl])-2'-deoxycytosine. In order to prove the absolute configuration of two chiral carbon atoms (C8, C9), the theoretical J coupling constant calculated from the plane position of the proton and the bond angle is used to compare with the experimental values (M. Karplus, Vicinal Proton Coupling in Nuclear Magnetic Resonance. *Journal of the American Chemical Society* 85, 2870-2871 (1963)), and P1 is inferred to have the (8S, 9S) configuration and P2 has the (8R, 9S) configuration.

Therefore, the structural formula of P1/P2 determined according to two-dimensional nuclear magnetic resonance and density functional theory is shown in FIG. 4B. P1 and P2 are stereoisomers with chiral differences only at the C8 position.

Embodiment 3. Source Analysis of Glycerol Group on 5mC

In order to investigate the source of the glycerol group added to 5mC, the present inventors first wanted to confirm whether it was derived from a protein or small molecule compound co-purified with Cmd1. After *E. coli* was cultured using $^{13}$C-labeled glucose as the sole carbon source, Cmd1 was purified for enzymatic activity reaction. After mass spectrometry analysis of the obtained reaction product P1/P2, the present inventors found that the molecular weight did not increase, indicating that the glycerol group was derived from an in vitro enzymatic activity reaction system (FIG. 6A). After screening for the components in the reaction system, the present inventors found that vitamin C (VC) is essential in the Cmd1 enzymatic activity reaction, not only acting as a reducing agent and promoting enzymatic activity in traditional Tet and other dioxygenase experiments (FIGS. 6B, 6D). On the other hand, 2-OG, as a cofactor required for many dioxygenases, may or may not be present in the enzymatic activity reaction of Cmd1 (FIGS. 6B, 6C). Therefore, the present inventors examined the molecular weight of P1/P2 produced by the reaction of VC with all six carbons labeled with $^{13}$C, and found that it was increased by 3 compared with the original. Further experiments with VC with a single carbon atom labeled with $^{13}$C revealed that C4-C6 on VC directly transferred to 5mC to form a new modification (FIG. 7). Moreover, the C-6 carbon atom on the VC corresponds to C-10 on P1, and C-5 on VC corresponds to C-9 of P1. In addition, the use of VC analogues, including D-isoascorbic acid, etc., can not directly replace VC for enzymatic activity experiments. These experimental results indicate that VC participates in the enzymatic activity reaction of Cmd1 (6E-G) as a direct reaction substrate. It is worth mentioning that a ferrous ion $Fe^2$ is also required in the reaction of Cmd1 (FIG. 6H). However, certain analogues of VC can also participate in the enzymatic activity reaction of Cmd1 as a direct or indirect reaction substrate, and exert the same effect as VC, and these analogues include: dehydroascorbic acid (which is indirectly involved in the reaction after being reduced by DTT), etc. (FIG. 6E).

Next, the present inventors examined the function of oxygen in the Cmd1 enzymatic activity reaction, conducted experiments in an oxygen-free glove box filled with nitrogen, and found that the enzymatic activity of Cmd1 was inhibited under anaerobic conditions. If oxygen is bubbled into the reaction flask, the enzymatic activity of Cmd1 can be normalized (FIG. 8A). However, oxygen and oxygen atoms in water were not transferred to the reaction product P1, further indicating that the increased atomic composition in P1 was derived from VC (FIG. 8B).

Referring to the reaction principle of the conventional dioxygenase, the present inventors also proposed the expected reaction mechanism of Cmd1 (FIG. 8C). In this mode pattern, VC replaces 2-OG and coordinates with Fe (II), the reactive group formed by oxidative decarboxylation deprives 5mC of methyl hydrogen atom, and the formed 5mC free radical causes homolysis of the coordination intermediate of Fe(II) and carboxylic acid, finally resulting in formation of P-modified nucleosides and by-product glyoxylic acids. In order to verify this reaction mechanism, the present inventors first need to detect the production of reaction by-products of VC. Using gas chromatography (GC-MS) experiments, the present inventors confirmed that after the reaction using $^{13}$C—VC, CO 2 was produced from the C-1 position of VC (FIG. 8D). In order to detect the formation of glyoxylic acid, the present inventors added 2,4-dinitrophenylhydrazine (DNP) to the reaction product of Cmd1 for derivatization, and the derivative product was detected by LC-MS. During the experiment, the present inventors found that C-2 and C-3 in VC were converted to glyoxylic acid using $^{13}$C—VC (FIG. 8E).

Example 4. In Vivo Enzymatic Activity Reaction

The present inventors have demonstrated that in an in vitro enzymatic activity reaction, Cmd1 catalyzes 5mC to form two new modifications P1/P2, and this embodiment demonstrates that this reaction process also occurs in the genome of *Chlamydomonas* cells.

Using a triple quadrupole mass spectrometer, the present inventors tested the genomic DNA base composition of six different strains of *Chlamydomonas*. The presence of P-modified bases can be detected in these strains, accounting for about 10-35 parts per million of C, and accounting for about 0.2% of 5mC (FIGS. 9A, 9B).

In order to confirm that the P-modified base was also catalyzed by Cmd1 in *Chlamydomonas*, the present inventors prepared a Cmd1-knockdown algal strain. Using artificially prepared microRNAs (amiRNAs), several strains with a knockdown efficiency of 70%-80% were obtained (FIG. 10).

Mass spectrometry results showed that in the genome of these algal strains, the content of P-modified bases was reduced by about 35%, and the corresponding content of 5mC was increased by about 17% (FIGS. 9C, 9D). After culturing *Chlamydomonas* with 5-azacytidine, an inhibitor of methyltransferase, the present inventors found that the content of 5mC in a genome was reduced by more than 50%, and consistently, the content of the P-modified base was also lowered by around 13%, indicating that in the genome, the P-modified base is also derived from 5mC (FIGS. 9E, 9F).

Embodiment 5. Function of VC-Derived 5mC New Modification (P Modification) and Single Base Level Detection 1. Reporter Gene Expression Assay Showing P Modification Inhibiting Gene Expression Using the method of the luciferase reporter gene, the present inventors found that the P modification strongly inhibits the expression of the reporter gene. The pCpGL-CMV-firefly reporter plasmid was used, and the plasmid contained a CpG site only in the CMV promoter region. After the present inventors have methylated the reporter plasmid in vitro using M.SssI methyltransferase, a reporter plasmid which is highly methylated in the CMV promoter region can be obtained. Further, after treatment with the Cmd1 enzyme, a reporter plasmid containing P modification in the CMV promoter region was obtained. This reporter plasmid was transfected into HEK293T cells and compared to unmodified common plasmids and 5mC reporter plasmids. The present inventors have found that the gene expression of the reporter plasmid containing P modification was significantly inhibited, and cannot be activated by Tet and TDG-mediated pathway with active demethylation of DNA, as shown in FIG. 12A.

2. P-Modified Single-Base Detection

In order to study the site-specific distribution of VC-derived new modifications in the genome, as well as its potential functions, and at the same time with the consideration of the need for analysis of various cytosine modifications in nucleic acid molecules, the present inventors designed a single-base detection method based on P modification, as shown in FIGS. 12B, C, D.

As shown in FIG. 12B, this is a combined Tet dioxygenase oxidation-bisulfite-seq method, that is, firstly, 5mC, 5hmC and 5fC in DNA are oxidized to 5caC by Tet dioxygenase, whereas the P modification could not be deaminized by bisulfite treatment because it could not be oxidized by Tet, and therefore, 5mC (appearing in the form of T) and P modification (appearing in the form of C) can be clearly distinguished by bisulfite-seq.

In the absence of P modification in DNA, the following methods can be used to distinguish between 5mC and 5hmC: firstly, DNA was treated with Cmd1, and 5mC was converted to P modification, whereas 5hmC stayed the same. Further, 5hmC was oxidized to 5caC (5caC can be converted by bisulfite deamination) using Tet dioxygenase, thereby distinguishing 5mC from 5hmC.

The pattern of the P-modified base in bisulfite-seq is the same as that of 5mC, and 5mC to which a glycerol group is attached to cannot be further oxidized by Tet dioxygenase to a base suitable for deamination like 5mC. Therefore, this Tet-oxidized bisulfite-seq (Tet-Oxi-BS-Seq) method can be used to distinguish P modification from 5mC.

The feature of Cmd1 catalyzing the reaction of 5mC with VC to form new modified products, can be used in the latest DNA sequencing technique to detect the content and distribution of 5mC.

3. The Effect of P Modification on Enzyme Cleavage

Enzyme digestion experiments also found that Cmd1-mediated P modification affects the cleavage activity of the restriction endonuclease MspI (recognizing CCGG sequence) on 5mC-DNA. MspI can cleave DNA containing 5mC modification, but after conversion to P modification by Cmd1 reaction, the function of MspI is repressed, as shown in FIG. 13.

DISCUSSION

As described above, the present inventors have found that a Tet homologous protein (Cmd1) of *Chlamydomonas* can catalyze the reaction of 5mC in the genome with a glycerol group composed of C4-C6 on VC to generate a new DNA modification. As a very important nutrient in many living organisms, VC is considered to serve as a reducing agent in a variety of physiological processes, for example, in the process of epigenetic modification reprogramming, the enzymatic activity of Tet and histone demethylase is promoted by maintaining the stability of $Fe^{2+}$ (M. A. Esteban, D. Pei, Vitamin C Improves the Quality of Somatic Cell Reprogramming. *Nature genetics* 44, 366-367 (2012); J. Du, J. J. Cullen, G. R. Buettner, Ascorbic Acid: Chemistry, Biology and the Treatment of Cancer. *Bba-Rev Cancer* 1826, 443-457 (2012)). The transfer of C4-C6 and hydroxyl groups on the chain of VC involves the cleavage and remodeling of C—C single bonds, and such reactions have never been reported in organic chemistry (FIG. 11). Although the chemical mechanism involved is not fully understood, it is at least certain that there is a large difference from the traditional dioxygenase-mediated oxidation reaction mechanism, especially when 2-OG does not play a role in the Cmd1 reaction, and there is also no binding site for 2-OG on the Cmd1 protein sequence. In the broader family of dioxygenases that depend on $Fe^{2+}$/2-OG, the enzyme for the synthesis of ethylene, ACC oxidase, has been shown to require VC rather than 2-OG as a reducing agent. Future knowledge of detection of the reaction by-products of VC and the role of $Fe^{2+}$ can help the present inventors better understand the reaction mechanism. The present inventors' experiments also predicted the existence of a new function of VC other than redox regulation, and suggested the possibility of interaction between DNA modifications and metabolites.

The function of the new DNA modification produced by the VC reaction in *Chlamydomonas* still need to be studied. However, at least the increased 5mC level observed by the present inventors from the Cmd1-knockdown algae strain suggests that Cmd1 may play a role in regulating the level of 5mC, just as the role of Tet dioxygenase in mammals. Further mass spectrometry results show that several other organisms, including mammals, which are evolutionarily similar to *Chlamydomonas reinhardtii*, may not have such P-modified bases or have low levels of modification. Using the method of the luciferase reporter gene, the present inventors have found that P modification strongly inhibits the expression of a reporter gene at least in mammalian cells (FIG. 12A).

In order to study the site-specific distribution of VC-derived new modifications in the genome, the present inventors designed a single-base detection method based on P modification (FIGS. 12B, C, D). The pattern of the P-modified base in bisulfite-seq is the same as that of 5mC. When a glycerol group is attached to 5mC, it cannot be further oxidized by Tet dioxygenase. Therefore, the Tet-oxidized bisulfite-seq method can be used to distinguish P from 5mC. Of course, the new product produced by the reaction of 5mC with VC catalyzed by Cmd1 can also be used in the latest DNA sequencing to detect the content of 5mC.

In addition, the reaction mechanism involved in Cmd1 enzymatic activity can also promote the further understanding and discussion of the existing organic chemistry theory, and contribute to the design of new organic chemistry experiments, including the extension of carbon chains and the addition of polyhydroxy groups. Further research may also promote the present inventors' transformation of the Cmd1 protein, thereby achieving goals of regulating gene expression in cells and designing specific epigenetic drugs, etc.

All documents mentioned in the present application are hereby incorporated by reference, just as each document is cited separately as a reference. Moreover, it should be understood that after reading the above teaching contents of the present invention, a person skilled in the art would make various changes or modifications on the present invention, these equivalent forms falling within the scope of the appended claims of the present application.

The invention claimed is:

1. A method for adding a glyceryl group to a methyl group of 5-methylcytosine of a methylated nucleic acid, comprising: treating the methylated nucleic acid with a Cmd1 enzyme, so that the glyceryl group is added to the methyl group of 5-methylcytosine of the methylated nucleic acid; the Cmd1 enzyme comprises: (a) a polypeptide of an amino acid sequence of SEQ ID NO: 1; (b) a polypeptide derived from (a), being formed by subjecting the amino acid sequence of SEQ ID NO: 1 to substitution, deletion or addition of one or more amino acid residues, and having a function of the polypeptide of (a); or (c) a polypeptide derived from (a), having more than 60% homology to the polypeptide sequence defined in (a) and having a function of the polypeptide of (a); and in the sequences defined in (b) and (c), based on the amino acid sequence of SEQ ID NO: 1, the 330th position is A, the 345th position is H, the 347th position is D, and the 350th position is D.

2. The method of claim 1, wherein a glyceryl group-containing compound is used as a glyceryl group donor.

3. The method of claim 2, wherein the glyceryl group-containing compound is vitamin C or an analogue thereof.

4. The method of claim 2, wherein the glyceryl group-containing compound is vitamin C or an analogue thereof; and the glyceryl group is a glyceryl group on vitamin C or an analogue thereof.

5. The method of claim 1, wherein in a reaction system in which the methylated nucleic acid is treated with the Cmd1 enzyme, a ferrous ion is present as a cofactor.

6. The method of claim 1, wherein the methylated nucleic acid is treated with the Cmd1 enzyme, thereby forming a product selected from the following:

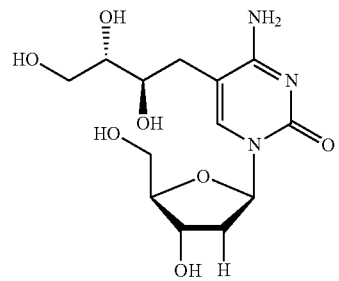

-continued

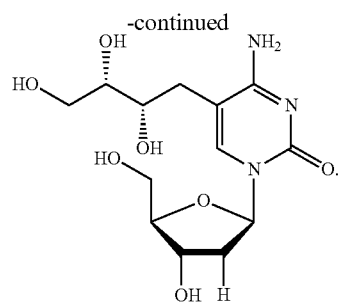

7. The method of claim 1, wherein the Cmd1 enzyme is a Cmd1 enzyme derived from algae.

8. A method for adding a glyceryl group to a methyl group of 5-methylcytosine of a methylated nucleic acid, comprising: treating the methylated nucleic acid with an up-regulator of a Cmd1 enzyme, so that the glyceryl group is added to the methyl group of 5-methylcytosine of the methylated nucleic acid; the Cmd1 enzyme comprises: (a) a polypeptide of an amino acid sequence of SEQ ID NO: 1; (b) a polypeptide derived from (a), being formed by subjecting the amino acid sequence of SEQ ID NO: 1 to substitution, deletion or addition of one or more amino acid residues, and having a function of the polypeptide of (a); or (c) a polypeptide derived from (a), having more than 60% homology to the polypeptide sequence defined in (a) and having a function of the polypeptide of (a); and in the sequences defined in (b) and (c), based on the amino acid sequence of SEQ ID NO: 1, the 330th position is A, the 345th position is H, the 347th position is D, and the 350th position is D; the up-regulator of the Cmd1 enzyme is an expression vector expressing the Cmd1 enzyme.

9. The method of claim 8, wherein the glyceryl group is attached to a carbon atom of the methyl group of 5-methylcytosine via a carbon-carbon single bond.

10. The method of claim 3, wherein the vitamin C analogue comprises dehydroascorbic acid.

11. The method of claim 4, wherein the vitamin C analogue comprises dehydroascorbic acid.

* * * * *